United States Patent
Van Houweling et al.

(10) Patent No.: US 12,385,869 B2
(45) Date of Patent: *Aug. 12, 2025

(54) SOIL MOISTURE AND NUTRIENT SENSOR SYSTEM

(71) Applicant: NutriProbe, LLC, Urbandale, IA (US)

(72) Inventors: Don Van Houweling, Perry, IA (US); Bradley G. Rathje, Bennet, NE (US); Arthur Henry Pickworth, Humpty Doo (AU)

(73) Assignee: NUTRIPROBE, LLC, Urbandale, IA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/672,231

(22) Filed: May 23, 2024

(65) Prior Publication Data
US 2024/0310315 A1 Sep. 19, 2024

Related U.S. Application Data

(63) Continuation of application No. 17/086,533, filed on Nov. 2, 2020, now Pat. No. 12,130,252.
(Continued)

(51) Int. Cl.
*G01N 27/22* (2006.01)
*G01K 13/00* (2021.01)
*G01N 33/24* (2006.01)

(52) U.S. Cl.
CPC .......... *G01N 27/223* (2013.01); *G01K 13/00* (2013.01); *G01N 27/221* (2013.01); *G01N 33/24* (2013.01); *G01N 33/245* (2024.05)

(58) Field of Classification Search
CPC .... G01N 27/223; G01N 27/221; G01N 33/24; G01N 2033/245; G01K 13/00; G01K 1/26
See application file for complete search history.

(56) References Cited

U.S. PATENT DOCUMENTS

| 10,330,660 B2 | 6/2019 | Ellegaard |
| 10,935,537 B2 | 3/2021 | Sointula |

(Continued)

FOREIGN PATENT DOCUMENTS

WO 2009049361 A1 4/2009

*Primary Examiner* — Lee E Rodak
*Assistant Examiner* — Zannatul Ferdous
(74) *Attorney, Agent, or Firm* — Christopher A. Proskey; BrownWinick Law Firm

(57) ABSTRACT

A soil moisture and fertility sensor system is presented that includes an elongated probe having a plurality of sensor modules positioned along the length of the probe. Each sensor module includes a co-located sensors configured to take a moisture, temperature, and fertility measurements at varying depths of the soil. The probe is configured for wireless communication. The probe is configured to take moisture measurements, temperature measurements and/or nutrient measurements at different times so as to prevent interference between measurements. The probe includes a plurality of receptacles that receive the fertility sensor assembly cartridge that may be inserted into and removed from a receptacle so as to facilitate end-of-life replacement. In one arrangement, the fertility sensor assembly includes a reference sensor and a plurality of nutrient sensors that are each configured to sense the presence of a specific nutrient.

22 Claims, 16 Drawing Sheets

Related U.S. Application Data

(60) Provisional application No. 62/930,182, filed on Nov. 4, 2019.

(56) References Cited

U.S. PATENT DOCUMENTS

| | | |
|---|---|---|
| 11,297,875 B2 | 4/2022 | Aughton |
| 2009/0242425 A1* | 10/2009 | Kamath ............. A61B 5/14532 |
| | | 205/792 |
| 2009/0302870 A1 | 12/2009 | Paterson |
| 2010/0301877 A1 | 12/2010 | Paterson |
| 2017/0020091 A1 | 1/2017 | McCoid |
| 2017/0023541 A1 | 1/2017 | Ellegaard |
| 2019/0159415 A1* | 5/2019 | Bertram ............... A01G 27/003 |
| 2019/0187086 A1* | 6/2019 | Burkey ................ H04W 84/20 |
| 2021/0127605 A1 | 5/2021 | Aughton |

\* cited by examiner

SOIL MOISTURE AND NUTRIENT SENSOR SYSTEM

CROSS-REFERENCE TO RELATED APPLICATIONS

The present application is a continuing patent application of U.S. patent application Ser. No. 17/086,533 filed on Nov. 2, 2020 and titled SOIL MOISTURE AND NUTRIENT SENSOR SYSTEM, which claims priority to U.S. Provisional Application No. 62/930,182 filed on Nov. 4, 2019 and titled SOIL MOISTURE AND NUTRIENT SENSOR SYSTEM, entirety of each of which is hereby incorporated by reference herein in its entirety, including any figures, tables, or drawings or other information.

FIELD OF THE DISCLOSURE

This disclosure relates to agriculture. More specifically and without limitation, this disclosure relates to systems and methods of sensing moisture and nutrients in soil.

OVERVIEW OF THE DISCLOSURE

Demands bestowed upon present day farmers are increasing by the day. Due to the cost of machinery, land, inputs, energy and labor, coupled with increasingly strict environmental demands, modern farmers must be vigilant to minimize inputs while maximizing yield while being as sustainable and environmentally friendly as possible.

The success of any crop largely depends upon the crop having access to adequate moisture as well as adequate nutrients during the crop's life cycle. Despite the importance of moisture and nutrients, presently there is no convenient and cost effective way to comprehensively monitor moisture and nutrients across a farm field.

Currently, farmers are forced to monitor in-season moisture and nutrients largely through a manual process. Many farmers simply drive around and/or walk through their fields to visually inspect the health of the crops. While this is somewhat effective, this method is labor intensive, time consuming, not-comprehensive and often leads to inconsistent and/or unscientific opinion-based results that are often not actionable in a timely manner.

This visual inspection process may be supplemented by the collection of soil samples and/or tissue samples which are then sent to a lab to be scientifically analyzed. Soil sampling and tissue sampling provides more-scientific results than simply visually inspecting the crop. However, soil sampling and tissue sampling is extremely expensive, extremely time consuming and from a practical standpoint simply cannot be performed in a comprehensive manner across a large farm or field. As such, soil sampling and tissue sampling, at best, provides a farmer with a few data points from which the farmer must make drastic assumptions that are extrapolated across their entire farm or field.

Both visual inspection and tissue sampling suffer from the same problem in that they are backward looking. That is, these processes require the effects of moisture levels and nutrient levels to appear in the crops, which is a trailing indicator. Therefore, this information only allows the farmer to be reactive instead of proactive. In addition, by the time the effects of moisture levels and nutrient levels appear in the crops often times irreparable damage and time loss has occurred that results in yield loss and suboptimal growth.

To compensate for this lack of information or lack of timely information, many farmers are forced to over-apply various nutrients and/or moisture so to ensure the crops have access to adequate nutrients and/or moisture throughout the growing season. This over application results in excess cost of inputs. In addition, the over-application of nutrients results in nutrient runoff that results in high nitrate readings in downstream sources of drinking water as well as offsite contamination which has been linked to algae blooms in lakes and rivers and the Gulf of Mexico.

As such, there is a need for an improved soil moisture and nutrient sensor system for agricultural use.

Thus, it is a primary object of the disclosure to provide a soil moisture and nutrient sensor system that improves upon the state of the art.

Another object of the disclosure is to provide a soil moisture and nutrient sensor system that is more environmentally friendly than existing systems and methods.

Yet another object of the disclosure is to provide a soil moisture and nutrient sensor system that is more efficient than existing systems and methods.

Another object of the disclosure is to provide a soil moisture and nutrient sensor system that is safer to use than existing systems and methods.

Yet another object of the disclosure is to provide a soil moisture and nutrient sensor system that provides comprehensive moisture data across a field or farm.

Another object of the disclosure is to provide a soil moisture and nutrient sensor system that provides comprehensive moisture data at varying depths.

Yet another object of the disclosure is to provide a soil moisture and nutrient sensor system that provides comprehensive nutrient data across a field or farm.

Another object of the disclosure is to provide a soil moisture and nutrient sensor system that provides comprehensive nutrient data at varying depths.

Yet another object of the disclosure is to provide a soil moisture and nutrient sensor system that provides real-time data.

Another object of the disclosure is to provide a soil moisture and nutrient sensor system that provides actionable data.

Yet another object of the disclosure is to provide a soil moisture and nutrient sensor system that provides leading-indicator data.

Another object of the disclosure is to provide a soil moisture and nutrient sensor system that allows a farmer to be proactive instead of reactive.

Yet another object of the disclosure is to provide a soil moisture and nutrient sensor system that allows a farmer to maximize output.

Another object of the disclosure is to provide a soil moisture and nutrient sensor system that allows a farmer to minimize inputs.

Yet another object of the disclosure is to provide a soil moisture and nutrient sensor system that allows a farmer to optimize inputs and outputs.

Another object of the disclosure is to provide a soil moisture and nutrient sensor system that gives a farmer unprecedented visibility to soil moisture and nutrients.

Yet another object of the disclosure is to provide a soil moisture and nutrient sensor system that improves yields.

Another object of the disclosure is to provide a soil moisture and nutrient sensor system that reduces costs.

Yet another object of the disclosure is to provide a soil moisture and nutrient sensor system that is relatively inexpensive.

Another object of the disclosure is to provide a soil moisture and nutrient sensor system that is simple to use.

Yet another object of the disclosure is to provide a soil moisture and nutrient sensor system that can be used to sense nutrients for an entire growing season.

Another object of the disclosure is to provide a soil moisture and nutrient sensor system that has replaceable nutrient sensors.

Yet another object of the disclosure is to provide a soil moisture and nutrient sensor system that is wireless.

Another object of the disclosure is to provide a soil moisture and nutrient sensor system that is battery powered.

Yet another object of the disclosure is to provide a soil moisture and nutrient sensor system that helps a farmer meet increasingly strict environmental regulations.

Another object of the disclosure is to provide a soil moisture and nutrient sensor system that is easy to use.

Yet another object of the disclosure is to provide a soil moisture and nutrient sensor system that is easy to implement.

Another object of the disclosure is to provide a soil moisture and nutrient sensor system that has a robust design.

Yet another object of the disclosure is to provide a soil moisture and nutrient sensor system that provides charts and graphs of soil moisture and soil nutrients.

Another object of the disclosure is to provide a soil moisture and nutrient sensor system that provides a farmer with increased confidence in their decisions.

Yet another object of the disclosure is to provide a soil moisture and nutrient sensor system that provides accurate soil moisture readings.

Another object of the disclosure is to provide a soil moisture and nutrient sensor system that provides accurate soil nutrient readings.

Yet another object of the disclosure is to provide a soil moisture and nutrient sensor system that allows for the measurement of multiple nutrients.

Another object of the disclosure is to provide a soil moisture and nutrient sensor system that normalizes moisture and nutrient readings with temperature.

Yet another object of the disclosure is to provide a soil moisture and nutrient sensor system that provides co-located moisture, temperature and nutrient readings at various depths.

Another object of the disclosure is to provide a soil moisture and nutrient sensor system that is cost effective to use.

Yet another object of the disclosure is to provide a soil moisture and nutrient sensor system that can be used with any crop.

Another object of the disclosure is to provide a soil moisture and nutrient sensor system that can be used with any nutrient.

Yet another object of the disclosure is to provide a soil moisture and nutrient sensor system that provides highly repeatable results.

Another object of the disclosure is to provide a soil moisture and nutrient sensor system that has a robust design.

Yet another object of the disclosure is to provide a soil moisture and nutrient sensor system that provides highly accurate results.

Another object of the disclosure is to provide a soil moisture and nutrient sensor system that has a long useful life.

Yet another object of the disclosure is to provide a soil moisture and nutrient sensor system that is easy to install.

Another object of the disclosure is to provide a soil moisture and nutrient sensor system that has relatively few components.

Yet another object of the disclosure is to provide a soil moisture and nutrient sensor system that has a minimum number of parts.

Another object of the disclosure is to provide a soil moisture and nutrient sensor system that minimized nutrient runoff.

Yet another object of the disclosure is to provide a soil moisture and nutrient sensor system that is environmentally friendly.

Another object of the disclosure is to provide a soil moisture and nutrient sensor system that improves a farmer's efficiency.

Yet another object of the disclosure is to provide a soil moisture and nutrient sensor system that saves a farmer time.

Another object of the disclosure is to provide a soil moisture and nutrient sensor system that that provides scientific information regarding soil moisture and nutrients.

These and other objects, features, or advantages of the present disclosure will become apparent from the specification, claims and drawings.

SUMMARY OF THE DISCLOSURE

A soil moisture and fertility sensor system is presented that includes an elongated probe having a plurality of sensor modules positioned along the length of the probe. Each sensor module includes a co-located moisture sensor assembly, temperature sensor assembly and fertility sensor assembly that take a moisture measurement, a temperature measurement and a fertility measurement at varying depths of the soil. The probe includes an on-board power source, which is at least one battery, and a communication module that facilitates wireless communication. The probe is configured to take moisture measurements, temperature measurements and/or nutrient measurements at different times so as to prevent interference between measurements. The probe includes a plurality of receptacles that receive the fertility sensor assembly therein which is formed on a cartridge that may be inserted into and removed from a receptacle so as to facilitate end-of-life replacement. In one arrangement, the fertility sensor assembly includes a reference sensor and a plurality of nutrient sensors that are each configured to sense the presence of a specific nutrient. In this way, use of this system provides unprecedented soil moisture and nutrient information.

DETAILED DESCRIPTION OF THE DISCLOSURE

Figure 1:
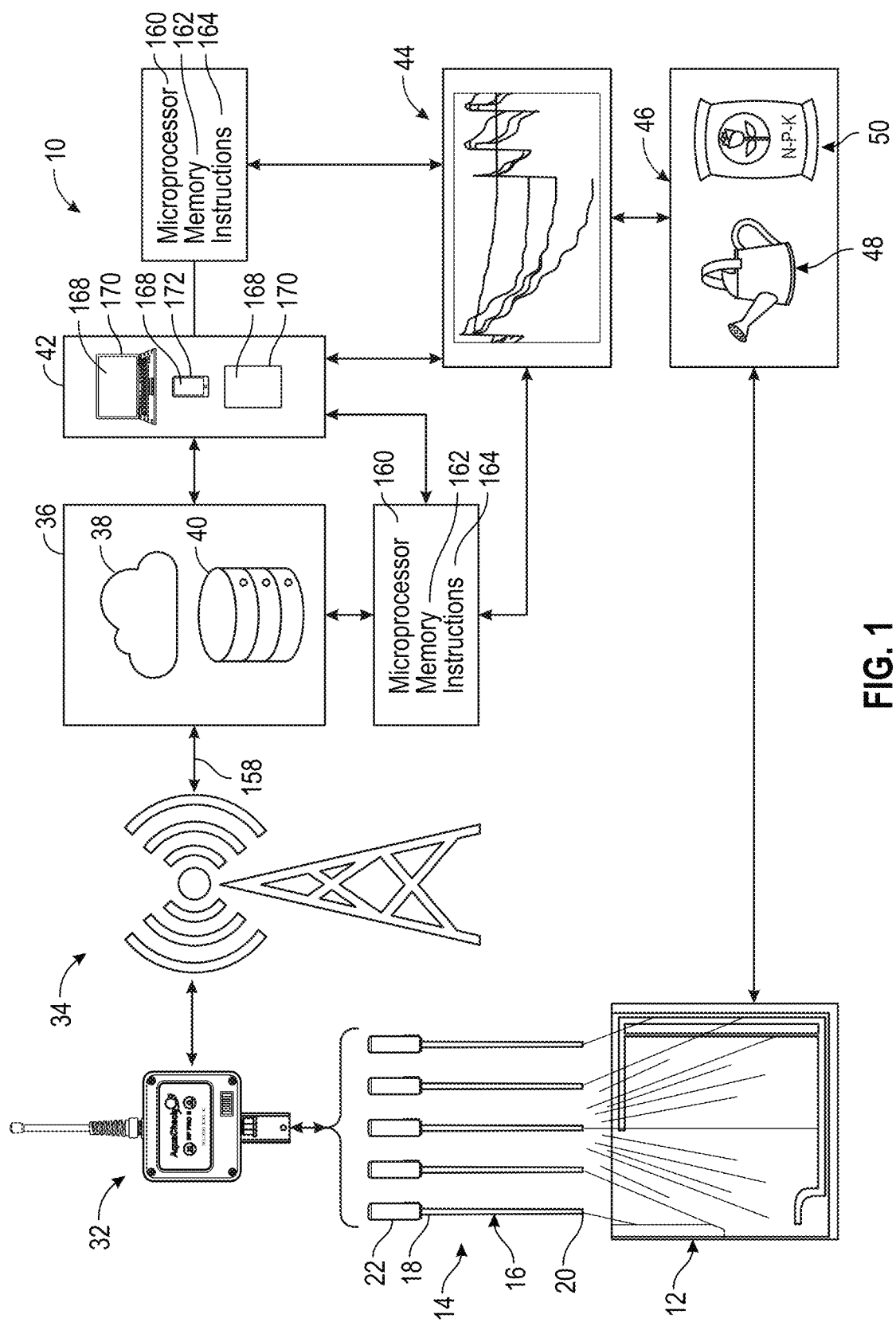
FIG. 1 shows a diagram of a soil moisture and fertility sensor system, in accordance with one or more embodiments.

In the following detailed description of the embodiments, reference is made to the accompanying drawings which form a part hereof, and in which is shown by way of illustration specific embodiments in which the disclosure may be practiced. The embodiments of the present disclosure described below are not intended to be exhaustive or to limit the disclosure to the precise forms in the following detailed description. Rather, the embodiments are chosen and described so that others skilled in the art may appreciate and understand the principles and practices of the present disclosure. It will be understood by those skilled in the art that various changes in form and details may be made without departing from the principles and scope of the invention. It is intended to cover various modifications and similar arrangements and procedures, and the scope of the appended claims therefore should be accorded the broadest interpretation so as to encompass all such modifications and similar arrangements and procedures. For instance, although aspects and features may be illustrated in or described with reference to certain figures or embodiments, it will be appreciated that features from one figure or embodiment may be combined with features of another figure or embodiment even though the combination is not explicitly shown or explicitly described as a combination. In the depicted embodiments, like reference numbers refer to like elements throughout the various drawings.

It should be understood that any advantages and/or improvements discussed herein may not be provided by various disclosed embodiments, or implementations thereof. The contemplated embodiments are not so limited and should not be interpreted as being restricted to embodiments which provide such advantages or improvements. Similarly, it should be understood that various embodiments may not address all or any objects of the disclosure or objects of the invention that may be described herein. The contemplated embodiments are not so limited and should not be interpreted as being restricted to embodiments which address such objects of the disclosure or invention. Furthermore, although some disclosed embodiments may be described relative to specific materials, embodiments are not limited to the specific materials or apparatuses but only to their specific characteristics and capabilities and other materials and apparatuses can be substituted as is well understood by those skilled in the art in view of the present disclosure.

It is to be understood that the terms such as "left, right, top, bottom, front, back, side, height, length, width, upper, lower, interior, exterior, inner, outer, and the like as may be used herein, merely describe points of reference and do not limit the present invention to any particular orientation or configuration.

As used herein, the term "or" includes one or more of the associated listed items, such that "A or B" means "either A or B". As used herein, the term "and" includes all combinations of one or more of the associated listed items, such that "A and B" means "A as well as B." The use of "and/or" includes all combinations of one or more of the associated listed items, such that "A and/or B" includes "A but not B," "B but not A," and "A as well as B," unless it is clearly indicated that only a single item, subgroup of items, or all items are present. The use of "etc." is defined as "et cetera" and indicates the inclusion of all other elements belonging to the same group of the preceding items, in any "and/or" combination(s).

As used herein, the singular forms "a," "an," and "the" are intended to include both the singular and plural forms, unless the language explicitly indicates otherwise. Indefinite articles like "a" and "an" introduce or refer to any modified term, both previously-introduced and not, while definite articles like "the" refer to a same previously-introduced term; as such, it is understood that "a" or "an" modify items that are permitted to be previously-introduced or new, while definite articles modify an item that is the same as immediately previously presented. It will be further understood that the terms "comprises," "comprising," "includes," and/or "including," when used herein, specify the presence of stated features, characteristics, steps, operations, elements, and/or components, but do not themselves preclude the presence or addition of one or more other features, characteristics, steps, operations, elements, components, and/or groups thereof.

It will be understood that when an element is referred to as being "connected," "coupled," "mated," "attached," "fixed," etc. to another element, it can be directly connected to the other element, and/or intervening elements may be present. In contrast, when an element is referred to as being "directly connected," "directly coupled," "directly engaged" etc. to another element, there are no intervening elements present. Other words used to describe the relationship between elements should be interpreted in a like fashion (e.g., "between" versus "directly between," "adjacent" versus "directly adjacent," "engaged" versus "directly engaged," etc.). Similarly, a term such as "operatively", such as when used as "operatively connected" or "operatively engaged" is to be interpreted as connected or engaged, respectively, in any manner that facilitates operation, which may include being directly connected, indirectly connected, electronically connected, wirelessly connected or connected by any other manner, method or means that facilitates desired operation. Similarly, a term such as "communicatively connected" includes all variations of information exchange and routing between two electronic devices, including intermediary devices, networks, etc., connected wirelessly or not. Similarly, "connected" or other similar language particularly for electronic components is intended to mean connected by any means, either directly or indirectly, wired and/or wirelessly, such that electricity and/or information may be transmitted between the components.

It will be understood that, although the ordinal terms "first," "second," etc. may be used herein to describe various elements, these elements should not be limited to any order by these terms unless specifically stated as such. These terms are used only to distinguish one element from another; where there are "second" or higher ordinals, there merely must be a number of elements, without necessarily any difference or other relationship. For example, a first element could be termed a second element, and, similarly, a second element could be termed a first element, without departing from the scope of example embodiments or methods.

Similarly, the structures and operations discussed herein may occur out of the order described and/or noted in the figures. For example, two operations and/or figures shown in succession may in fact be executed concurrently or may sometimes be executed in the reverse order, depending upon the functionality/acts involved. Similarly, individual operations within example methods described below may be executed repetitively, individually or sequentially, to provide looping or other series of operations aside from single operations described below. It should be presumed that any embodiment or method having features and functionality described below, in any workable combination, falls within the scope of example embodiments.

As used herein, various disclosed embodiments may be primarily described in the context of soil measurements. However, the embodiments are not so limited. It is appreciated that the embodiments may be adapted for use in various other sensor applications, which may be improved by the disclosed structures, arrangements and/or methods. The system is merely shown and described as being used in the context of soil measurements for ease of description and as one of countless examples.

System 10:

With reference to the figures, a soil moisture and fertility sensor system 10 (or simply system 10), and method of use is presented. System 10 is formed of any suitable size, shape and design and is configured to facilitate the periodic measurement of moisture and nutrients in a farm field 12 at various locations around the field and at various depths.

To be clear, while the term fertility sensor and the term soil fertility is used herein, these terms are intended to also mean soil chemistry. That is, various constituents of soil that are important to the soil's health and ability to sustain crops may not necessarily be considered nutrients which may include sodium, pH, among others. As used herein the term fertility sensor and the term soil fertility as used herein is intended to cover all soil constituents including soil chemistry. As such, the soil moisture and fertility sensor system 10 presented herein is intended to sense soil moisture, soil fertility and soil chemistry.

In the arrangement shown, as one example, soil moisture and fertility sensor system 10 includes: a plurality of probes 14 having a tube 16 having an upper end 18 and a lower end 20, a head 22, a plurality of sensor modules 24 having a moisture sensor assembly 26, a temperature sensor assembly 28 and fertility sensor assembly 30, a gateway 32, a cellular tower 34, the internet 36, the cloud 38, a database 40, a computing device 42, displays 44 which are used to control inputs 46, such as water 48 and nutrients 50 which are applied to the field 12, among other components, pieces, systems and features, as is further described herein.

Field 12:

In the arrangement shown, as one example, soil moisture and fertility sensor system 10 is shown in use with one or more fields 12. Field 12 is formed of any suitable size, shape and design and is configured to facilitate the growth of crops. In the arrangement shown, as one example, field 12 is a conventional farm field that consists of naturally deposited soil that is exposed to the elements such as that used to grow conventional crops such as corn, soybeans, wheat, hay, alfalfa, oats, cotton, vegetables, grapes, or any other crop. However, use of system 10 in association with a conventional farm or field 12 is only one of countless examples of use and is not intended to be limiting. Instead, it is hereby contemplated that system 10 is intended to be used not just with conventional farms and fields 12, but also wherever crops or plants are grown. Additional examples include use with greenhouses, potted plants, orchards, vineyards, gardens, arboretums, grow houses, or any other place where plants or crops are grown.

Probe 14:

In the arrangement shown, as one example, soil moisture and fertility sensor system 10 includes the use of one or more probes 14. Probe 14 is formed of any suitable size, shape and design and is configured to be inserted in the soil of the field 12. Probe 14 is configured to sense moisture, temperature and nutrients in the soil of field 12 at various depths so as to provide a farmer with real-time actionable leading-indicator information so that the farmer may adjust the inputs 46, such as water 48 and nutrients 50 before the lack of moisture and/or nutrients negatively affect plant growth. In the arrangement shown, as one example, probe 14 includes a tube 16 that extends a length from an upper end 18 to a lower end 20 and includes a head 22 connected to the upper end of tube 16. However, any other configuration is hereby contemplated for use.

Tube 16 (of Probe 14):

In the arrangement shown, as one example, probe 14 includes a tube 16. Tube 16 is formed of any suitable size, shape and design and is configured to serve as the main housing of probe 14 and serves to house and hold and connect the other components of probe 14 while providing protection to the other components of probe 14. Tube 16 is configured to be inserted within the soil of field 12 so as to facilitate the taking of moisture, temperature and nutrient measurements.

In the arrangement shown, as one example, tube 16 extends a length from an upper end 18 to a lower end 20. Tube 16 may extend any length. It is hereby contemplated that tube 16 may extend only a few inches to several feet, such as three feet, four feet, five feet, six feet, seven feet, eight feet, nine feet, ten feet, or more, or any range or length therein.

In the arrangement shown, as one example, tube 16 is formed of a generally cylindrical tube-shaped member having a hollow interior, a pointed tip at its lower end 20 and head 22 connected at its upper end 18.

The pointed tip at lower end 20 helps to facilitate easy insertion of probe 14 into the soil of field 12. The hollow interior is configured to receive, house and hold the other components of probe 14 as is further described herein.

While a cylindrical shaped tube 16 is shown, a cylindrical tube 16 is only one of countless possible shapes for tube 16. Any other shaped member is hereby contemplated for use as tube 16 such as a square tube, a rectangular tube, an oval-shaped tube, a T-shaped member, an I-shaped member or any other shaped member.

In the arrangement shown, as one example, tube 16 is formed of a single continuous member so as to eliminate seams that could allow for the infiltration of water and contaminants into the hollow interior of tube 16. In an alternative arrangement, tube 16 is formed of a plurality of components that are connected together either in a removable manner, such as by screwing, bolting, clamping, snap-fitting or the like, or in a permanent manner such as by welding, gluing, or the like, or any combination thereof. Additionally or alternatively, in one or more arrangements tube 16 may be filled with a resin or another filler to restrict moisture or soil from entering the probe and damaging components.

In one arrangement, the pointed tip at lower end 20 is formed as a continuous monolithic member with tube 16. In an another arrangement, pointed tip at lower end 20 is assembled onto tube 16 either in a removable manner, such as by screwing, bolting, clamping, snap-fitting or the like, or in a permanent manner such as by welding, gluing, or the like, or any combination thereof.

In the arrangement shown, as one example, tube 16 includes a plurality of sensor modules 24 that are positioned in spaced relation to one another along the length of tube 16. In this way, when tube 16 is inserted vertically into the soil the spaced sensor modules 24 are positioned at different depths of the soil and the sensor modules 24 measure characteristics of the soil at different depths. In an arrangement shown, tube 16 of probe 14 is approximately twenty four inches long and includes sensor modules 24 at six positions along tube 16. However, embodiments are not so limited. Rather, it is contemplated that in various arrangement, tube may be made to be any length and may include any number of sensor modules 24 at any number different positions along tube 16.

In the arrangement shown, as one example, tube 16 includes an upper-most sensor module 24 position a short distance below head 22, a lower-most sensor module 24 positioned a distance above the tip at the lower end 20, and a plurality of sensor modules 24 positioned at equal-spacing between the upper-most sensor module 24 and the lower-most sensor module 24.

In the arrangement shown, as one example, tube 16 includes a receptacle 52 positioned at the location of each sensor module 24. In the arrangement shown, as one example, receptacle 52 is formed as an opening in the sidewall of tube 16 that is configured to receive a fertility sensor assembly 30 therein as is further described herein.

In one arrangement, tube 16 is formed of a plastic material or non-metallic material that provides structural rigidity for protection purposes as well as being impermeable by water. In one arrangement a PVC (Polyvinyl Chloride) material is used, however any other non-metallic material is hereby contemplated for use. Alternatively, a metallic material may be used such as aluminum, iron, steel or any other metallic material or alloy.

Head 22 (of Probe 14):

In the arrangement shown, as one example, probe 14 includes a head 22. Head 22 is formed of any suitable size, shape and design and is configured to connect to the upper end 18 of tube 16 and enclose the upper end of probe 14. In one arrangement, head 22 houses and/or holds and/or facilitates connection to all or a portion of various components of probe 14 such as lead 54, controller assembly 56 including body 58, processing circuit 60, memory 62 having instructions 64, such as software 66 and/or code 68, a communication module 70 having antenna 72 and communication circuit 74, an electrically connected power source 76, among other components and parts and systems. When all or part of these or other components of probe 14 are not housed or held in head 22 they are housed or held within tube 16, or alternatively these components may be housed or held within a telemetry unit 33 that is electrically connected to probe 14 through lead 54.

Figure 2:
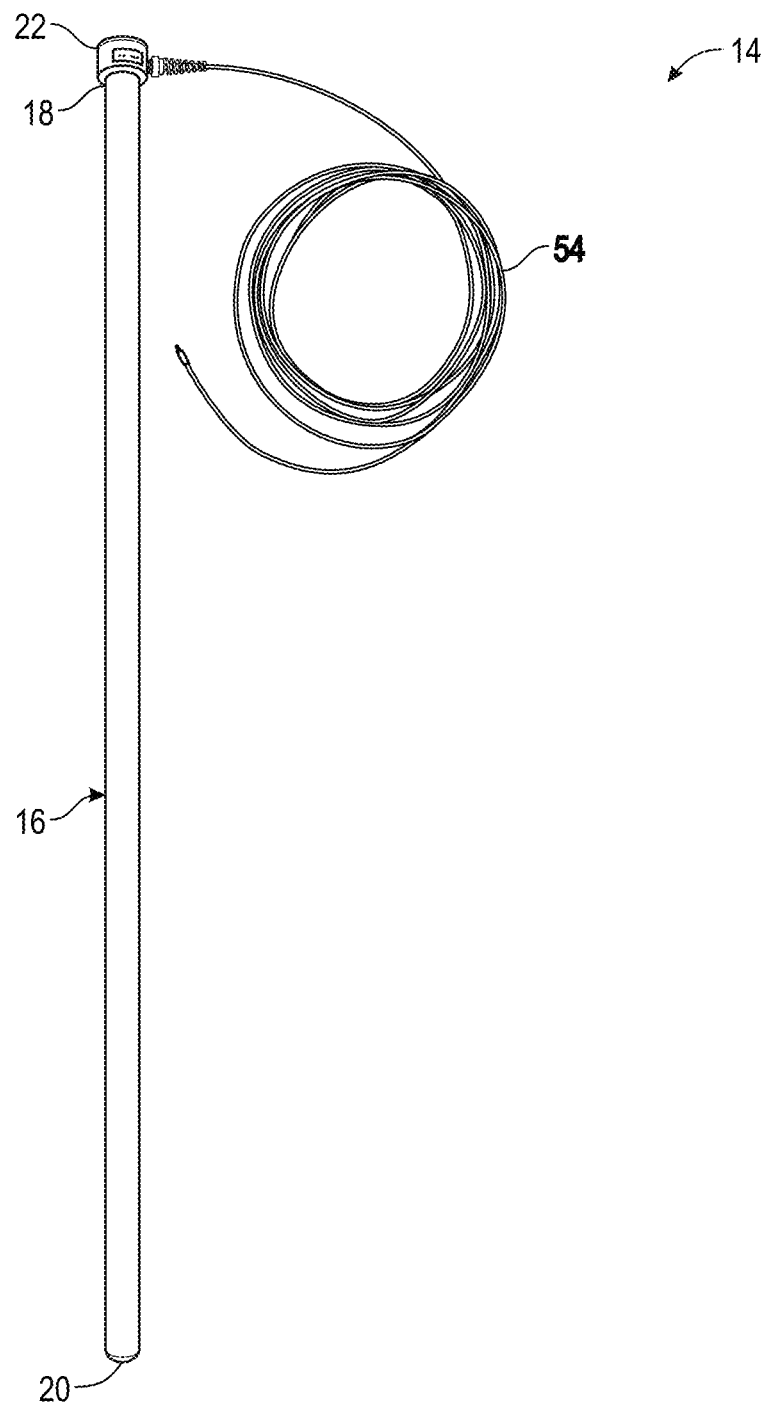
FIG. 2 shows a front view of a wired probe for use in a soil moisture and fertility sensor system, in accordance with one or more embodiments.

With reference to FIG. 2, a wired probe 14 is presented. In this arrangement, head 22 facilitates connection to a lead 54. Lead 54 is formed of any suitable size, shape and design and is configured to facilitate the wired transmission of information and/or power to and/or from probe 14 and gateway 32 or another component of the system 10. Lead 54 may be a power cable, a coaxial cable, an Ethernet cable, an optical cable, a proprietary cable, or any other cable, lead, wire or the like or any combination thereof. Lead 54 facilitates the wired connection to another component of the system such as gateway 32 (or telemetry unit 33), another probe 14, an external power source such as a battery, a solar panel or line power, the internet, an intranet, or any other component of the system or combination thereof. In this arrangement, lead 54 extends into head 22 and electrically connects to some or all electronic components of probe 14 either directly or indirectly.

Figure 3:
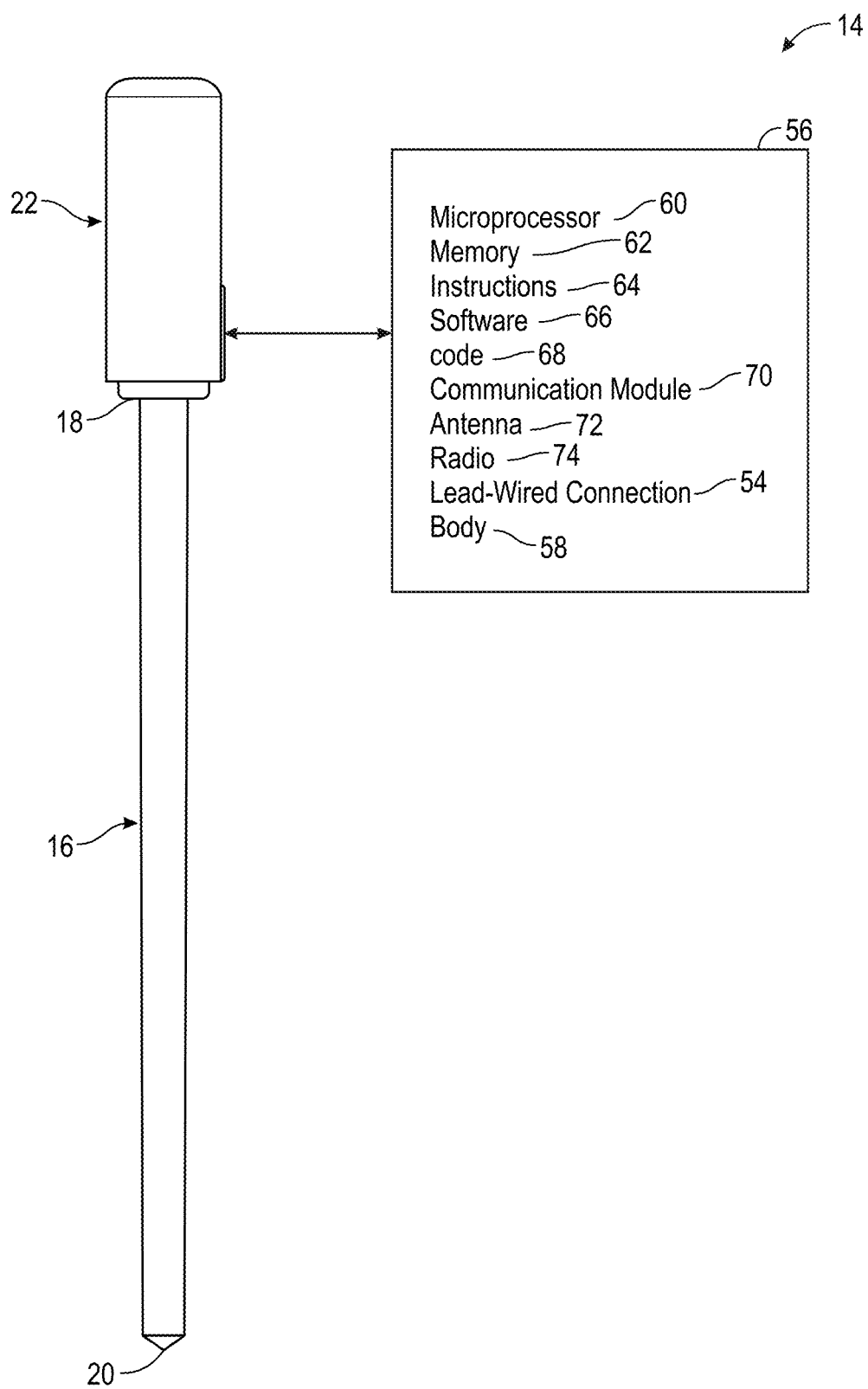
FIG. 3 shows a front view of a wireless probe for use in a soil moisture and fertility sensor system, in accordance with one or more embodiments.
Figure 4:
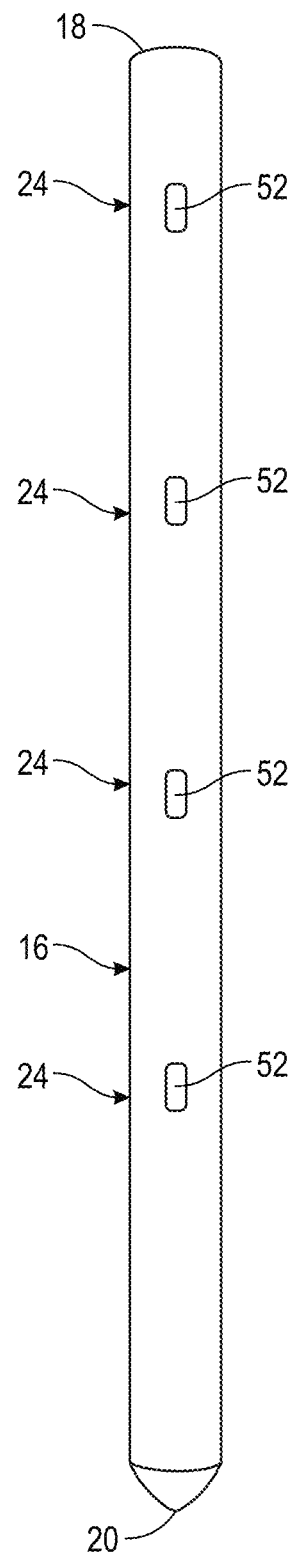
FIG. 4 shows a front view of a tube of a probe for use in a soil moisture and fertility sensor system, in accordance with one or more embodiments; the view showing the tube with four sensor modules.
Figure 5:
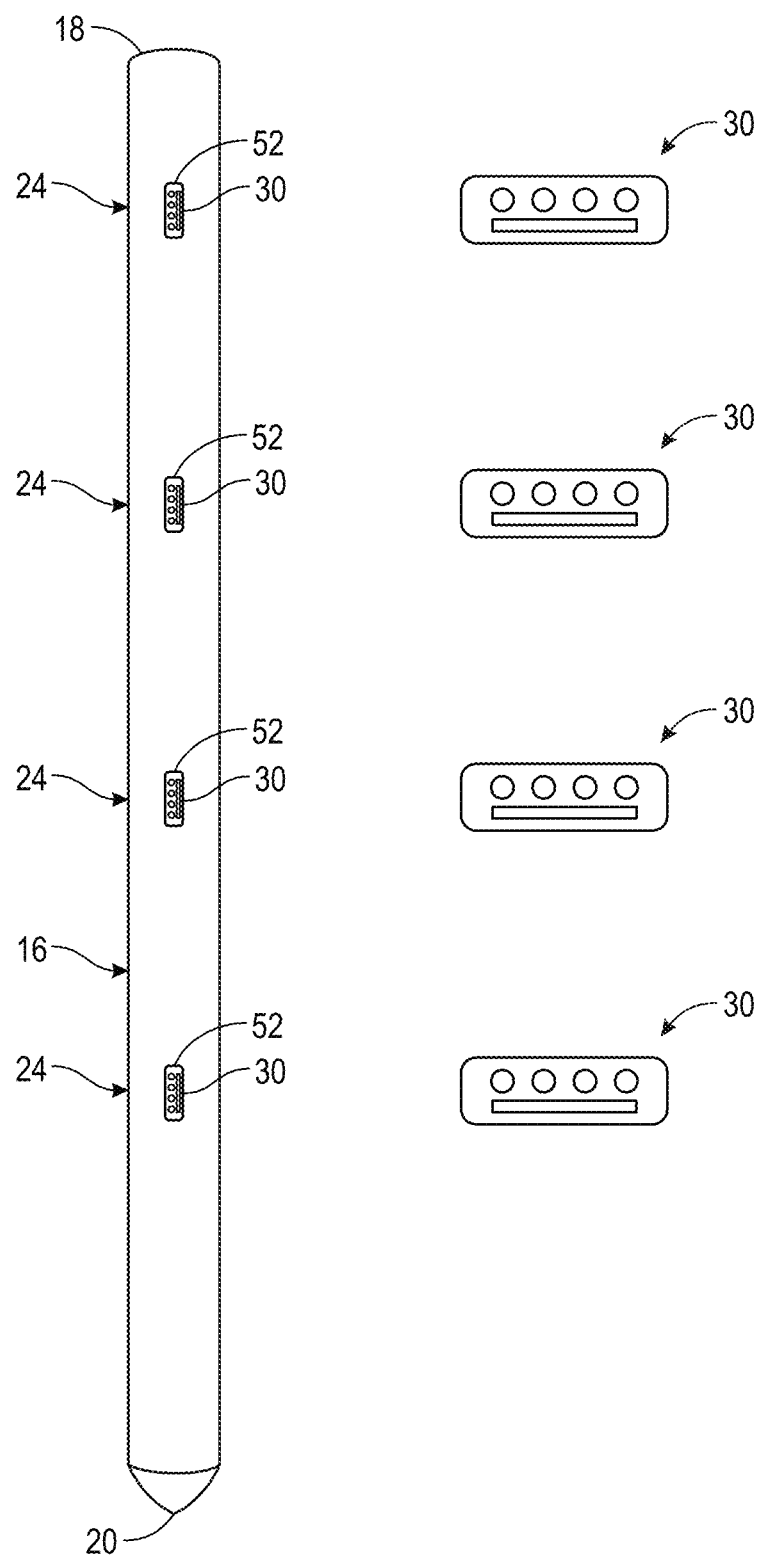
FIG. 5 shows a front view of a tube of a probe for use in a soil moisture and fertility sensor system, in accordance with one or more embodiments; the view showing the tube with four sensor modules; the view showing a closeup of nutrition sensor assemblies of the sensor modules.

With reference to FIG. 3, a wireless probe 14 is presented. In this arrangement, head 22 is formed to house and hold all or a portion of communication module 70. Communication module 70 is formed of any suitable size, shape and design and is configured to facilitate wireless communication of probe 14 with gateway 32, cellular tower 34, the internet 36, the cloud 38, the farmer's or user's computing device 42 or any other component of the system 10.

In the arrangement shown, as one example, communication module 70 is any device or combination of devices that facilitate wireless communication of probe 14. In the arrangement shown, as one example, communication module 70 includes an antenna 72 and communication circuit 74 that facilitates wireless communication of probe 14. In various arrangements, communication circuit 74 may be configured to communicate using any protocol such as Random Phase Multiple Access (RPMA), 802.11/Wi-Fi, Wi-Max, Bluetooth, Bluetooth Low Energy, UltraWideband (UWB), ZigBee, Zwave, GSM/EDGE, UMTS/HSPA+/HSDPA, CDMA, LTE, and/or FM/VHF/UHF networks or any other communication medium and/or protocol. A transmitter receiver is used for communication circuit 74 if one way communication is utilized in that a receiver is configured to transmit information only. In contrast, a transceiver is used for communication circuit 74 if two-way communication is utilized in that a transceiver sends as well as receives information.

Various arrangements may utilize various different network topologies to facilitate connection between probes 14 and/or gateway 32 to facilitate communication or data from probes to database 40. In the arrangement shown, as one example, a set of probes 14 are connected to a single gateway 32 in a star topology. However, embodiments are not so limited. Rather, it is contemplated that probes 14 and gateway(s) 32 may be connected in any network topology including but not limited to tree, mesh, star, ring, daisy chain, hybrid, and/or any other topology. In one or more arrangements, communication modules 70 of probes 14 and/or gateway are configured to form an adhoc network for communication of data.

Communication module 70, including communication circuit 74, is connected to an antenna 72. Antenna 72 is any device that facilitates the transmission and/or reception of the over-the-air signals, and may include a monopole antenna, dipole antenna, a loop antenna, a fractal antenna, or any other form of an antenna or combination thereof. Antenna 72 is configured to receive wireless signals from another component of the system 10, such as gateway 32, computing device 42 or another component, transmits these signals to the receiver/transceiver of communication module 70. Communication module 70 processes these signals and then transmits these processed signals to processing circuit 60, which processes these signals according to instructions stored in memory 62 as is further described herein.

In one arrangement, head 22 is configured to sit just above the ground. That is, in this arrangement the lower end of head 22 is positioned at or just above the ground and the head 22 extends upward therefrom. This arrangement ensures wireless signals may be transmitted out of head 22 without interference of the ground. However, this arrangement exposes head 22 to the potential for damage, such as being run over by equipment, as head 22 protrudes out of the ground.

In another arrangement, head 22 is configured to be inserted into the ground. That is, in this arrangement the upper end of head 22 is positioned at (or flush with) or just above or just below the ground. This arrangement protects head 22 as head 22 is submerged into the ground and therefor if probe 14 is driven over, head 22 and probe 14 may not be damaged or may be somewhat protected from damage. However, this arrangement may present challenges as wireless signals may be inhibited from being transmitted out of head 22 due to interference of the ground. In addition, special attention may be needed to ensure that head 22 is properly sealed to prevent the infiltration of water and contaminants if head 22 is to be submerged within the soil.

Controller Assembly 56, Processing Circuit 60, Memory 62, Instructions 64:

In the arrangement shown, as one example, probe 14 includes a controller assembly 56. Controller assembly 56 is formed of any suitable size, shape and design and is configured to control operation of some or all of the electronic components of the probe 14. In the arrangement shown, as one example, controller assembly 56 includes one or more processing circuits 60, memory 62, or one or more memory devices, and instructions 64, which may be in the form of software 66 or code 68, among multiple other components and systems.

In the arrangement shown, as one example, controller assembly 56 is electrically connected, either directly or indirectly, through wired connections, or wirelessly, to other electronic components positioned throughout probe 14 such as communication module 70, sensor modules 24, power source 76 and the like. In various arrangements, controller assembly 56 may be configured to communicate with the various other electronic components using any protocol such as Serial Data Interface 12 (SDI-12), UART, Serial Peripheral Interface, PCI/PCIe, Serial ATA, ARM Advanced Microcontroller Bus Architecture (AMBA), USB, Firewire, 802.11/Wi-Fi, Wi-Max, Bluetooth, Bluetooth Low Energy, Ultra Wideband (UWB), ZigBee, Zwave, GSM/EDGE, UMTS/HSPA+/HSDPA, CDMA, LTE, and/or FM/VHF/UHF networks or any other communication medium and/or protocol.

In the arrangement shown, as one example, controller assembly 56 includes stored instructions 64, such as operational routines, that controller assembly 56 executes. Alternatively and/or in addition, in the arrangement shown, as one example, controller assembly 56 receives information and/or instructions 64 from gateway 32, a user-controlled computing device 42, a cellular tower 34, the internet 36, the cloud 38, or another component of the system 10. Controller assembly 56 processes this information according to instructions 64 stored in memory 62 and then outputs commands thereby controlling operation of the probe 14.

In one or more arrangements, controller assembly 56 is configured to operate sensors modules 24 to take periodic measurements during operation. In one example arrangement, controller assembly 56 is configured to operate sensors modules 24 to take soil measurements every 15 minutes. However, embodiments are not so limited. Rather it is contemplated that various embodiments may be configured to take soil measurements at any interval or measurement schedule.

In various different arrangements, controller assembly 56 may be configured to use communication circuit 74 to communicate soil measurements to gateway 32, cellular tower 34, the internet 36, the cloud 38, the farmer's or user's computing device 42 and or any other component of the system 10 at various intervals. In one or more arrangements, as one example, controller assembly 56 may be configured to use communication circuit 74 to communicate soil measurements in real time. Additionally or alternatively, in one or more arrangements, controller assembly 56 may be configured to store soil measurements in memory 62 and communicate multiple measurements to gateway 32, cellular tower 34, the internet 36, the cloud 38, the farmer's or user's computing device 42 and or any other component of the system 10 at a less frequent interval (e.g., hourly, daily, weekly, monthly, or any other interval). In this manner controller assembly 56 may save power by operating communication circuit 74 less frequently. Processing circuit 60 is formed of any suitable size, shape and design and is configured to receive and process information and output commands. In one or more arrangements, for example, such processing circuits includes a circuit specifically configured and arranged to carry out one or more of these or related operations/activities. For example, processing circuit 60 may be discreet logic circuits or programmable logic circuits configured and arranged for implementing these operations/activities, as shown in the figures, and/or described herein. In certain embodiments, such a programmable circuit may include one or more programmable integrated circuits (e.g., field programmable gate arrays and/or programmable ICs). Additionally or alternatively, such a programmable circuit may include one or more processing circuits (e.g., a computer, microcontroller, system-on-chip, smart phone, server, and/or cloud computing resources). For instance, computer processing circuits may be programmed to execute a set (or sets) of instructions (and/or configuration data). The instructions (and/or configuration data) can be in the form of firmware or software stored in and accessible from a memory 62 (circuit). Certain embodiments are directed to a computer program product (e.g., nonvolatile memory device), which includes a machine or computer-readable medium having stored thereon instructions which may be executed by a computer (or other electronic device) to perform these operations/activities.

Memory 62 is any form of information storage such as flash memory, ram memory, a hard drive, or any other form of memory or combination thereof. Memory 62 may be included as a part of or operably connected to processing circuit 60. Controller assembly 56 may be a single component that is located at a single physical location. Alternatively, controller assembly 56 may be formed of multiple electronic components that are separated but communicatively connected to one another that act in concert with one another.

Processing circuit 60 may be a single component that is located at a single physical location. Alternatively, processing circuit 60 may be formed of multiple electronic components that are separated but electrically connected to one another that act in concert with one another.

Memory 62 may be a single component that is located at a single physical location. Alternatively, memory 62 may be formed of multiple electronic components that are separated but communicatively connected to one another that act in concert with one another.

Processing circuit 60 and memory 62 may be a single joined component that is located at a single physical location, such as within head 22, within tube 16, or at any other location. Alternatively, processing circuit 60 and memory 62 may be formed of multiple electronic components that are separated but electrically connected to one another that act in concert with one another.

In one arrangement, controller assembly 56, which includes processing circuit 60, memory 62 and instructions 64, which may be in the form of software 66, code 68 or any other form of information, controls operation of probe 14. That is, in one arrangement, controller assembly 56 controls the operation of sensor modules 24 as well as the transmission of information through communication module 70, as is further described herein.

In one arrangement, wherein probe 14 is connected to telemetry unit 33 by lead 54, controller assembly 56 and some or all of the related components described herein (processing circuit 60, memory 62 and instructions 64, communication module 70, antenna 72, communication circuit 74, power source 76, and the like) are contained within telemetry unit 33 which is configured to communicate with gateway 32, the internet 36, the cloud 38, computing device 42 and/or another component of the system 10.

Sensor Modules 24:

In the arrangement shown, as one example, soil moisture and fertility sensor system 10 includes a plurality of sensor modules 24. Sensor modules 24 are formed of any suitable size, shape and design and are configured to facilitate the measurement of the moisture level, temperature, and/or nutrients in the soil surrounding probe 14.

In the arrangement shown, as one example, sensor modules 24 include a moisture sensor assembly 26, a temperature sensor assembly 28 and a fertility sensor assembly 30. In the arrangement shown, sensor modules 24 positioned along the length of tube 16 of probe 14 at equal spacing along the length of probe 14 such that when probe 14 is vertically inserted within the soil, the sensor modules 24 are positioned such that sensor assemblies 26, 28, and/or 30 measures characteristics of the soil at different depths.

In the arrangement shown, as one example, each of the sensor modules 24 include a co-located moisture sensor assembly 26, a temperature sensor assembly 28, and a fertility sensor assembly 30. By co-locating the moisture sensor assembly 26, the temperature sensor assembly 28 and the fertility sensor assembly 30 of each of the sensor modules 24 this ensures that accurate readings are being made of the soil moisture, temperature and fertility at the same or approximately the same position or vertical depth of the soil. In this way, the term co-locating is intended to mean located at approximately the same position on probe 14.

In one arrangement, the fertility sensor assembly 30 is positioned within or between the moisture sensor assembly 26 of each sensor module 24.

In the arrangement shown, as one example, every sensor module 24 includes a single co-located moisture sensor assembly 26, temperature sensor assembly 28 and fertility sensor assembly 30. However, it is hereby contemplated that each sensor module 24 may include any number of moisture sensor assemblies 26, such as one, two, three, four, five, six, seven, eight, nine or ten or more. However, it is hereby contemplated that each sensor module 24 may include any number of temperature sensor assemblies 28, such as one, two, three, four, five, six, seven, eight, nine or ten or more. However, it is hereby contemplated that each sensor module 24 may include any number of fertility sensor assemblies 30, such as one, two, three, four, five, six, seven, eight, nine or ten or more. Whether sensor module 24 includes one or more moisture sensor assemblies 26, temperature sensor assemblies 28 and/or fertility sensor assemblies 30, these moisture sensor assemblies 26, temperature sensor assemblies 28 and fertility sensor assemblies 30 are co-located within the sensor module 24, which means they are located within a narrowly defined area or space where the moisture sensor assemblies 26, temperature sensor assemblies 28 and fertility sensor assemblies 30 are located near one another so as to measure that soil at similar locations.

Moisture Sensor Assembly 26 (of Sensor Module 24):

In the arrangement shown, as one example, sensor modules 24 of soil moisture and fertility sensor system 10 include a moisture sensor assembly 26. Moisture sensor assembly 26 is formed of any suitable size, shape and design and is configured to measure the moisture content of the soil at the position of the moisture sensor assembly 26 which is co-located with the position of the temperature sensor assembly 28 and the fertility sensor assembly 30 of each sensor module 24.

Any form of a moistures sensor or moisture sensing system is hereby contemplated for use as moisture sensor assembly 26. In addition, while only one moisture sensor assembly 26 is shown in use with each sensor module 24, any number of moisture sensor assemblies 26 are hereby contemplated for use with each sensor module 24.

In the arrangement shown, as one example, moisture sensor assembly 26 is formed of what is known as a capacitance sensor. In electrical engineering, capacitive sensing (sometimes capacitance sensing) is a technology, based on capacitive coupling, that can detect and measure anything that is conductive or has a dielectric different from air. In the arrangement shown, as one example, when moisture sensor assembly 26 is a capacitive moisture sensor, moisture sensor assembly 26 includes a positive plate 78, a negative plate 80 and a space or dielectric 82 positioned between the positive plate 78 and the negative plate 80.

A capacitive moisture sensor works by measuring the changes in capacitance caused by the changes in the dielectric 82. A capacitive moisture sensor does not measure moisture directly (pure water does not conduct electricity well), instead it measures the ions that are dissolved in the moisture. These ions and their concentration can be affected by a number of factors, for example adding fertilizer for instance will decrease the resistance of the soil. Capacitive measuring basically measures the dielectric that is formed by the soil and the water is the most important factor that affects the dielectric.

Noncontact capacitive sensors work by measuring changes in an electrical property called capacitance. Capacitance describes how two conductive objects (positive plate 78 and negative plate 80) with a space between them (space or dielectric 82) respond to a voltage difference applied to the positive plate 78 and negative plate 80. When a voltage is applied to the positive plate 78 and negative plate 80, an electric field is created in the space or dielectric 82 between them causing positive and negative charges to collect on each of the positive plate 78 and negative plate 80.

In one arrangement, capacitive sensors use an alternating voltage which causes the charges to continually reverse their positions. The moving of the charges creates an alternating electric current which is detected by a sensor. The amount of current flow is determined by the capacitance, and the capacitance is determined by the area and proximity of the conductive objects. Larger and closer objects cause greater current than smaller and more distant objects. The capacitance is also affected by the type of nonconductive material in the space or dielectric 82 between the positive plate 78 and negative plate 80.

In the arrangement shown, capacitive-based moisture sensor assemblies 26 at different heights along tube 16 of probe 14 to measure moisture content at different soil depths. It has been surprisingly discovered that placement of capacitive-based moisture sensor assemblies 26 at positioned are separated by at least four inches avoids interference between capacitive-based moisture sensor assemblies 26 and improves sensitivity. However, it is contemplated that in one or more arrangements capacitive-based moisture sensor assemblies 26 may be separated by any distance along tube 16 of probe 14.

Capacitive measuring has some advantages. Namely, capacitive measuring avoids corrosion of the positive plate 78 and the negative plate 80. Capacitive measuring also gives a better reading of the moisture content of the soil as opposed to using a resistive soil moisture sensor. Capacitive measuring avoids corrosion of the positive plate 78 and the negative plate 80 since the positive plate 78 and the negative plate 80 of the capacitor are not exposed to the soil. As such, there is no corrosion of the positive plate 78 and the negative plate 80.

In the arrangement shown, as one example, positive plate 78 and negative plate 80 are formed of electrical conductors. In the arrangement shown, as one example, positive plate 78 and negative plate 80 are formed of electrical plates. In the arrangement shown, as one example, positive plate 78 and negative plate 80 are positioned within the hollow interior of tube 16 and have an exterior surface that is in engagement with or in close proximity to the interior surface of tube 16.

In the arrangement shown, as one example, positive plate 78 and negative plate 80 extend in a continuous and uninterrupted manner around the entire circumference of the interior surface of tube 16. That is, in this arrangement, positive plate 78 and negative plate 80 extend three hundred and sixty degrees around the probe 14, and/or around the interior surface of the hollow interior of tube 16.

In one arrangement, positive plate 78 and negative plate 80 are formed on and/or into an insert 84 that is configured to be inserted within the hollow interior of tube 16. In the arrangement shown, as one example, insert 84 extends a length between an upper end 86 and a lower end 88 and is sized and shaped to fit within the hollow interior of tube 16 with close and tight tolerances. In the arrangement shown, as one example, insert 84 has an exterior size and shape that closely matches the interior size and shape of tube 16. That is, when tube 16 is cylindrical in shape, insert 84 is cylindrical in shape; when tube 16 is square in shape, insert 84 is square in shape, and so on.

As the moisture level or humidity of the soil between the positive plate 78 and negative plate 80 changes, the measured capacitance changes. These changes in capacitance of the soil in the space or dielectric 82 between positive plate 78 and negative plate 80 are extrapolated using an algorithm to determine the true moisture content of the soil at the location of that particular sensor module 24. In one arrangement, the temperature measurement taken by the co-located temperature sensor assembly 28 is used in association with the capacitance measurement taken by the co-located moisture sensor assembly 26 to normalize the moisture measurement for that particular sensor module 24. This helps to take reduce or eliminate the affect that temperature has on capacitance readings.

In the arrangement shown, as one example, the temperature sensor assembly 28 and fertility sensor assembly 30 of each sensor module 24 are positioned between the positive plate 78 and negative plate 80 of the moisture sensor assembly 26. Or, said another way, in the arrangement shown, as one example, the temperature sensor assembly 28 and the fertility sensor assembly 30 of each sensor module 24 are positioned within the space or dielectric 82 of the moisture sensor assembly 26.

In an alternative arrangement, temperature sensor assembly 28 and fertility sensor assembly 30 of each sensor module 24 are positioned adjacent the positive plate 78 or negative plate 80 of the moisture sensor assembly 26. In an alternative arrangement, a temperature sensor assembly 28 is positioned on the outside of each of the positive plate 78 and negative plate 80. In an alternative arrangement, a fertility sensor assembly 30 is positioned on the outside of each of the positive plate 78 and negative plate 80.

Notably, while a single positive plate 78 and a single negative plate 80 is shown in use, any number of positive plates 78 and negative plates 80 are hereby contemplated for use. As one example, each moisture sensor assembly 26 may include a single positive plate 78 and two negative plates 80, one on each side of the positive plate 78. As another example, each moisture sensor assembly 26 may include a single negative plate 80 and two positive plates 78, one on each side of the negative plate 80. As another example, each moisture sensor assembly 26 may include a two positive plates 78 and two negative plates 80 which are adjacent each other. Any other number of positive plates 78 and negative plates 80 are hereby contemplated for use as is any other arrangement of these positive plates 78 and negative plates 80.

In one arrangement, moisture sensor assembly 26 uses Frequency Domain Reflectometry (FDR) or alternatively Time-Domain Reflectometry (TDR). These technologies do not measure actual soil moisture levels but soil tension, electro-conductivity, di-electric constant or resistance.

Temperature Sensor Assembly 28 (of Sensor Module 24):

In the arrangement shown, as one example, sensor modules 24 of soil moisture and fertility sensor system 10 include a temperature sensor assembly 28. Temperature sensor assembly 28 is formed of any suitable size, shape and design and is configured to measure the temperature of the soil at the position of the temperature sensor assembly 28 which is co-located with the position of the moisture sensor assembly 26 and the fertility sensor assembly 30 of each sensor module 24.

Any form of a temperature sensor or temperature sensing system is hereby contemplated for use as temperature sensor assembly 28. In addition, while only one temperature sensor assembly 28 is shown in use with each sensor module 24, any number of temperature sensor assemblies 28 are hereby contemplated for use with each sensor module 24.

In the arrangement shown, as one example, temperature sensor assembly 28 is formed of what is known as a thermometer, or a digital thermometer or an electronic thermometer. However, any other form of a temperature sensor is hereby contemplated for use including thermocouples, resistance temperature detectors (RTDs), thermistors, semiconductor based integrated circuits (ICs), and/or any other form of a temperature sensor.

Thermocouples are made by joining two dissimilar metal wires together. This causes a Seebeck Effect. The Seebeck Effect is a phenomenon in which a temperature difference of two dissimilar conductors produces a voltage difference between the two substances. It is this voltage difference that can be measured and used to calculate the temperature.

RTDs operate under the principle that as temperature changes, the resistance of any metal changes as well. This difference in resistance is what RTD temperature sensors are based on. An RTD is a resistor with well-defined resistance vs. temperature characteristics. Platinum is the most common and accurate material used to make RTDs.

Thermistors are similar to RTDs in that temperature changes cause measurable resistance changes. Thermistors are usually made from a polymer or ceramic material. In most cases, thermistors are cheaper but are also less accurate than RTDs. Most thermistors are available in two wire configurations. The NTC (Negative Temperature Coefficient) thermistor is the most commonly used thermistor for temperature measurement application. An NTC thermistor's resistance decreases as the temperature increases. Thermistors have a non-linear temperature resistance relationship. This requires a significant correction to interpret the data correctly.

Semiconductor based temperature sensor ICs come in two different types: local temperature sensor and remote digital temperature sensor. Local temperature sensors are ICs that measure their own die temperature by using the physical properties of a transistor. Remote digital temperature sensors measure the temperature of an external transistor.

In the arrangement shown, as one example, like positive plate 78 and negative plate 80, temperature sensor assembly 28 is formed as part of insert 84 and is positioned within the hollow interior of tube 16. In this way, tube 16 protects temperature sensor assembly 28. In one arrangement, as one example, temperature sensor assembly 28 includes a probe that extends outward from or is flush with the exterior surface of tube 16 so as to ensure direct contact with the soil to ensure accurate measurements.

In the arrangement shown, as one example, like fertility sensor assembly 30, temperature sensor assembly 28 is positioned within moisture sensor assembly 26. That is, in one arrangement, temperature sensor assembly is positioned between the positive plate 78 and negative plate 80 of moisture sensor assembly 26.

The temperature measurements provided by temperature sensor assemblies 28 are in and of themselves valuable information. In addition, in one arrangement, temperature measurements provided by temperature sensor assembly 28 are used to normalize the readings from moisture sensor assembly 26 and/or fertility sensor assembly 30. That is, the readings from temperature sensor assembly 28 and moisture sensor assembly 26 are used as inputs into an algorithm or program performed by processing circuit 60 of controller assembly 56 or another processing device or processing circuit of another component of the system 10 which normalizes the reading from moisture sensor assembly 26 to provide an accurate measurement of the moisture level in the soil. Similarly, the readings from temperature sensor assembly 28 and fertility sensor assembly 30 are used as inputs into an algorithm or program performed by processing circuit 60 of controller assembly 56 or another processing device or processing circuit of another component of the system 10 which normalizes the reading from fertility sensor assembly 30 to provide an accurate measurement of the nutrient level in the soil.

Fertility Sensor Assembly 30 (of Sensor Module 24):

In the arrangement shown, as one example, sensor modules 24 of soil moisture and fertility sensor system 10 include a fertility sensor assembly 30. Fertility sensor assembly 30 is formed of any suitable size, shape and design and is configured to measure one or more characteristics of the soil, such as various nutrient levels, ion levels, pH and/or other characteristics that relate to fertility and soil health and productivity.

Any form of a fertility sensor or fertility sensing system is hereby contemplated for use as fertility sensor assembly 30. In addition, while only one fertility sensor assembly 30 is shown in use with each sensor module 24, any number of fertility sensor assemblies 30 are hereby contemplated for use with each sensor module 24.

Cartridge 90:

In the arrangement shown, as one example, fertility sensor assembly 30 includes a cartridge 90. Cartridge 90 is formed of any suitable size, shape and design and is configured to fit within receptacle 52 of probe 14. Cartridge 90 is configured to be easily installed into receptacle 52 of probe 14 prior to use. Cartridge 90 is configured to be held within receptacle 52 of probe 14 during use. Cartridge 90 is configured to be easily removed from receptacle 52 after use and after cartridge 90 has exceeded its useful lifespan. That is, cartridge 90 is configured to be easily inserted within and removed from receptacle 52 so as to facilitate a removable and disposable fertility sensor assembly 30.

In the arrangement shown, as one example, cartridge 90 of fertility sensor assembly 30 includes a body 92. Body 92 of cartridge 90 of fertility sensor assembly 30 is formed of any suitable size, shape and design and is configured to be the main structural element of cartridge 90 and is configured to house and hold and connect the other components of cartridge 90 of fertility sensor assembly 30 while providing structural support and rigidity.

In the arrangement shown, as one example, body 92 is formed of a generally planar member having a generally flat exterior surface 94 and a generally flat interior surface 96 and an exterior peripheral edge 98. In the arrangement shown, as one example, exterior surface 94 and interior surface 96 extend in approximate parallel planar spaced relation to one another. In the arrangement shown, as one example, exterior peripheral edge 98 extends in an approximate perpendicular manner to the planes formed by exterior surface 94 and interior surface 96. In the arrangement shown, as one example, body 92 is generally rectangular shaped when viewed from above or below and includes generally straight sidewalls 100 that extend in approximate parallel spaced relation to one another and includes generally straight end walls 102 that extend in approximate parallel spaced relation to one another. In the arrangement shown, as one example, sidewalls 100 and end walls 102 extend in approximate perpendicular relation to one another thereby forming a generally square or rectangular shaped member.

In the arrangement shown, as one example, sidewalls 100 and end walls 102 connect to one another at rounded corners. Collectively, sidewalls 100, end walls 102, and the rounded corners positioned there between, form peripheral edge 98 of body 92 of cartridge 90 of fertility sensor assembly 30.

In the arrangement shown, as one example, body 92 is formed of a printed circuit board (PCB), a substrate, or another form of a device that provides structural rigidity as well as selective electrical connections and selective electrical isolations.

Sealing Member 104:

In the arrangement shown, as one example, cartridge 90 includes a sealing member 104. Sealing member 104 is formed of any suitable size, shape and design and is configured to allow for the insertion of cartridge 90 into receptacle 52, as well as facilitate removal of cartridge 90 from receptacle 52, as well as facilitate forming a seal between cartridge 90 of fertility sensor assembly 30 and receptacle 52 of probe 14.

In the arrangement shown, as one example, sealing member 104 is a flexible, compressible or otherwise malleable member that forms a seal between cartridge 90 and receptacle 52. In the arrangement shown, as one example, sealing member 104 is an O-ring that extends around the exterior peripheral edge 98 of body 92 of cartridge 90 in a continuous and uninterrupted manner. In one arrangement, body 92 includes a wall that extends rearward from interior surface 96 a distance. This wall may be formed as part of sealing member 104. Alternatively, this wall may be a separate component from sealing member 104. This wall provides alignment and additional surface area of engagement between the walls of receptacle 52 and the exterior peripheral edge 98 of cartridge 90 thereby providing increased sealing capabilities.

Electrical Contacts 106:

In the arrangement shown, as one example, cartridge 90 includes one or more electrical contacts 106 positioned in its interior surface 96 that electrically connect to one or more sensors in its exterior surface 94 through traces or leads that extend through body 92 of cartridge 90. These sensors include reference sensor 108 and nutrient sensors 110.

Electrical contacts 106 are formed of any suitable size, shape and design and are configured to facilitate the establishment of an electrical connection between cartridge 90 and the other components of probe 14. In the arrangement shown, as one example, electrical contacts 106 of cartridge 90 are sized and shaped to engage electrical contacts 112 in receptacle 52 of probe 14. In one arrangement, electrical contacts 106 of cartridge 90 are metallic and/or conductive pads that receive and/or engage electrical contacts 112 of receptacle 52 which may be formed of compressible electrical contacts, such as electrically conductive foams or "pogo pins" which are spring loaded metallic pins that facilitate the establishment of an electrical connection between two components. In an alternative arrangement, electrical contacts 106 of cartridge 90 may be formed of compressible electrical contacts, such as what are known as "pogo pins" which are spring loaded metallic pins that facilitate the establishment of an electrical connection between two components and electrical contacts 112 of receptacle 52 are metallic and/or conductive pads. The use of electrical contact pads on one of cartridge 90 and receptacle 52 and the use of compressible electrical contacts on the other of cartridge 90 and receptacle 52 facilitates the easy installation and removal of cartridge 90 into receptacle 52 while facilitating a secure and durable electrical connection between cartridge 90 and receptacle 52.

In one arrangement, when electrical contacts 106 of cartridge 90 are spring loaded pogo pins, when cartridge 90 is replaced, the pogo pins are replaced. This is beneficial as pogo pins do, overtime, wear out and break, this may be especially true when cartridge 90, and the attached pogo pins are exposed to moisture, dirt and other contaminants. And as such, by replacing cartridge 90 the pogo pins are replaced. This may provide durability, robustness, repeatability, and a long useful life.

Reference Sensor 108 and Nutrient Sensors 110:

In the arrangement shown, as one example, cartridge 90 includes at least one reference sensor 108 and at least one nutrient sensor 110 positioned in its exterior surface 94 that are each electrically connected to an electrical contact 106 in the interior surface 96 of cartridge 90. Reference sensor 108 and nutrient sensors 110 are formed of any suitable size, shape and design and are configured to sense or detect the concentration of various nutrients in the soil. In the arrangement shown, as one example, reference sensor 108 and nutrient sensors 110 are what are known as ion selective electrodes. An ion-selective electrode (ISE), also known as a specific ion electrode (SIE), is a transducer (or sensor) that converts the activity of a specific ion dissolved in a solution into an electrical potential. The voltage is theoretically dependent on the logarithm of the ionic activity, according to the Nernst equation.

In the arrangement shown, as one example, each cartridge 90 includes one reference sensor 108 and four nutrient sensors 110, however any number of reference sensors 108 and nutrient sensors 110 are hereby contemplated for use.

In the arrangement shown, as one example, reference sensor 108 and nutrient sensors 110 are formed of gold pads that are connected to the exterior surface 94 of cartridge 90. Gold pads, whether solid gold or plated gold, are useful in that gold does not oxidize. However, any other conductive material is hereby contemplated for use.

In the arrangement shown, as one example, reference sensor 108 is formed an elongated rectangular pad that extends along one side of cartridge 90. In the arrangement shown, as one example, reference sensor 108 extends the majority of the length of the end wall 102 to end wall 102 length of cartridge 90. However, any other length or shape or configuration is hereby contemplated for use.

In the arrangement shown, as one example, nutrient sensors 110 are formed of generally cylindrical shaped pads that are aligned along one side of cartridge 90, opposite reference sensor 108, in a row. In the arrangement shown, as one example, four nutrient sensors 110 are shown, adjacent reference sensor 108 and as such, nutrient sensors 110 are approximately one quarter the size of the reference sensor 108. However, any other length or shape or configuration is hereby contemplated for use.

In the arrangement shown, as one example, reference sensor 108 and nutrient sensors 110 include a polyimide layer 114 and a graphene layer 116.

Polyimide Layer 114 and Graphene Layer 116 and Perforations 118:

In the arrangement shown, as one example, reference sensor 108 and nutrient sensors 110 include a polyimide layer 114 and a graphene layer 116.

In the arrangement shown, as one example, polyimide layer 114 covers the entire exterior surface 94 of cartridge 90. In an alternative arrangement, polyimide layer 114 covers a portion of the exterior surface 94 of cartridge 90. In an alternative arrangement, polyimide layer 114 covers the entire surface of reference sensor 108 and nutrient sensors 110.

Polyimide (sometimes abbreviated PI) is a polymer of imide monomers. With their high heat-resistance, polyimides enjoy diverse applications in roles demanding rugged organic materials, e.g. high temperature fuel cells, displays, and various military roles. One example polyimide is Kapton, which is produced by condensation of pyromellitic dianhydride and 4,4'-oxydianiline.

In the arrangement shown, as one example, polyimide layer 114 serves as an electrical insulator to the conductive reference sensor 108 and nutrient sensors 110.

In the arrangement shown, as one example, polyimide layer 114 is formed of a Kapton tape. Kapton is a polyimide film developed by DuPont in the late 1960s that remains stable across a wide range of temperatures, from −269 to +400° C. (−452 to 752° F.; 4 to 673 K). Kapton is used in, among other things, flexible printed circuits (flexible electronics) and thermal blankets used on spacecraft, satellites, and various space instruments.

The chemical name for Kapton K and HN is poly (4,4'-oxydiphenylene-pyromellitimide). It is produced from the condensation of pyromellitic dianhydride and 4,4'-oxydiphenylamine. Kapton synthesis is an example of the use of a dianhydride in step polymerization. The intermediate polymer, known as a "poly(amic acid)", is soluble because of strong hydrogen bonds to the polar solvents usually employed in the reaction. The ring closure is carried out at high temperatures (200-300° C. (392-572° F.; 473-573 K)).

In the arrangement shown, as one example, polyimide layer 114 is applied to the exterior surface 94 of cartridge 90 as a Kapton tape. In this arrangement, an adhesive, or an adhesive layer is positioned between the polyimide layer 114 and the exterior surface 94 of cartridge 90 to ensure adhesion of the polyimide layer 114 to the exterior surface 94 of cartridge 90.

Any other form of material is hereby contemplated for use as polyimide layer 114, particularly any other form of material that can be converted into graphene.

In some arrangements, as one example, a plurality of perforations 118 or micro-perforations are formed in polyimide layer 114 prior to application of polyimide layer 114 onto the exterior surface 94 of cartridge 90. Perforations 118 are formed of any suitable size, shape and design and are formed of openings that extend through the polyimide layer 114 from its upper surface to its lower surface.

In the arrangement shown, as one example, perforations 118 are generally small circular openings in polyimide layer 114, however any other size, shape and design is hereby contemplated for use. In the arrangement shown, as one example, perforations 118 are placed in polyimide layer 114 above reference sensor 108 and nutrient sensors 110. In this way, when polyimide layer 114 is applied to the exterior surface 94 of cartridge 90, perforations 118 land on top of reference sensor 108 and nutrient sensors 110. In this way, the openings formed by perforations 118 provide access to the exterior surface of reference sensor 108 and nutrient sensors 110.

After polyimide layer 114 is applied to the exterior surface 94 of cartridge 90, sections 120 are treated with a laser. As the laser interacts with the exterior surface of polyimide layer 114 a layer of graphene, or graphene layer 116 is formed. In one arrangement a $CO_2$ laser is used to form graphene layer 116 from polyimide layer 114. However, any other form of a laser is hereby contemplated for use.

In one or more arrangements, copper traces are laid around the edge of the polyimide layer 114. The Lasing of the polyimide electronically welds the graphene (LIG) to the trace. These traces extend through body 92 of cartridge 90 to connect with electrical contacts 106 of cartridge 90, in which case perforations 118 may be omitted. The LIG and with copper trace creates a tighter hydrophobic seal, which may provide more accurate and more stable readings.

Forming graphene layer 116 by applying a laser to polyimide layer 114 is called Laser-induced Graphene (LIG). Laser-induced graphene (LIG) is a 3D porous material prepared by direct laser writing with a $CO_2$ or other laser on carbon materials in ambient atmosphere. This technique combines 3D graphene preparation and patterning into a single step without the need for wet chemical steps.

Graphene, the atomically-thin honeycomb carbon lattice, is a highly conducting 2D material whose exposed electronic structure offers a platform for chemical and biological sensing. Its biocompatible, flexible and chemically inert nature associated with the lack of dangling bonds, offers opportunities for direct interfacing with biological molecules. Combined with its exceptional electronic and optical properties, this promotes graphene as a unique platform for bioelectronics.

In one or more arrangements, LIG is produced by applying a laser over the carbon material in a nitrogen gas atmosphere. However, embodiments are not so limited. Rather it is contemplated that various arrangements may use other LIG formation techniques. For example, it has been surprisingly discovered two or more applications of a DPI laser at different power levels and/or or at different angles in a normal environment (no Nitrogen gas) generates a more highly conductive and robust sensor.

In one arrangement, the laser is applied in sections 120 of polyimide layer 114. That is, wherever the laser is applied, the upper surface or the exterior surface of polyimide layer 114 is converted into a layer of graphene or graphene layer 116. However, this graphene layer 116 is extremely thin, and does not extend all the way through polyimide layer 114. As such, despite the fact that graphene layer 116 is conductive, because of the underlying polyimide layer 114 the reference sensor 108 and nutrient sensors 110 positioned below the graphene layer 116 and polyimide layer 114 would remain insulated if it were not for perforations 118 that extend through polyimide layer 114.

In the arrangement shown, as one example, when reference sensor 108 is generally rectangular in shape, the section 120 covers the interior portion of reference sensor 108. That is, in this arrangement, the section 120 of reference sensor 108 is a slightly smaller rectangular shape that is positioned just inward a distance from the exterior peripheral edge of reference sensor 108. Similarly, in the arrangement shown, as one example, when nutrient sensors 110 are generally circular in shape, the section 120 covers the interior portion of nutrient sensors 110. That is, in this example arrangement, the section 120 of nutrient sensors 110 is a slightly smaller circular shape that is positioned just inward a distance from the exterior peripheral edge of nutrient sensors 110.

In the arrangement shown, as one example, when a laser is applied to sections 120 of polyimide layer 114, the upper surface or exterior surface of polyimide layer 114 is converted into graphene layer 116. This graphene layer 116 is conductive. In the arrangement shown, as one example, when a laser is applied to the edges of perforations 118 a graphene layer 116 is formed along the edges of perforations 118.

This graphene layer 116 along the edges of perforations 118 forms a conduit or connector or conductor from the graphene layer 116 in the exterior surface of polyimide layer 114 down to the reference sensor 108 or nutrient sensor 110 positioned below the polyimide layer 114. In addition to serving as an electrical connection to reference sensor 108 or nutrient sensor 110, the intersection at the lower end of perforations 118 is fused to the reference sensor 108 or nutrient sensor 110 when the laser is applied to polyimide layer 114 thereby forming a graphene layer 116. That is, when the laser hits the intersection of the lower end of the polyimide layer 114 of a perforation, a portion of the polyimide layer 114 and a portion of the material of the reference sensor 108 or nutrient sensor 110 are melted and/or mixed, and/or fused and/or welded together as the graphene layer 116 is formed thereby securely affixing the graphene layer 116, as well as the polyimide layer 114, to the underlying reference sensor 108 or nutrient sensor 110. This prevents delamination of the graphene layer 116, as well as the polyimide layer 114, from the underlying reference sensor 108 or nutrient sensor 110. This prevents electrical disconnection of the graphene layer 116 from the underlying reference sensor 108 or nutrient sensor 110. For lack of a better term, by providing perforations 118 in polyimide layer 114 and applying a laser to the polyimide layer 114 and forming a graphene layer 116 that fuses to the underlying reference sensor 108 or nutrient sensor 110 this plugs the graphene layer 116 into the underlying reference sensor 108 or nutrient sensor 110.

In the arrangement shown, as one example, each reference sensor 108 and nutrient sensor 110 include a plurality of perforations 118 within each section 120 of graphene layer 116 and as such, graphene layer 116 is electrically and physically connected to the underlying reference sensor 108 or nutrient sensor 110 at each perforation 118. In this way a graphene based electrode is formed or said another way, a graphene based sensor is formed. When ions come in direct contact with the graphene layer 116, the ions change the potential of the electrode by charge transfer, which is directly proportional to the ion concentration. These graphene based electrodes or graphene based sensors are substantially less expensive to manufacture in terms of fabrication as compared to comparable alternatives, and they are amenable to miniaturization, low-energy consumption, as well as diverse applications.

In the arrangement shown, reference sensor 108 is an open sensor in that it does not have an ion selective membrane 122 covering the reference sensor 108. As such, all ions are able to reach the reference sensor 108. This provides a constant reference potential, and potentiostat, which records the open circuit potential (OCP) which is used to normalize the readings from the nutrient sensors 110 which include an ion selective membrane 122.

As an alternative to forming graphene along the sides of a perforation 118 to form an electrical contact with the underlying reference sensor 108 or nutrient sensor 110, in one arrangement perforations 118 are filled with a conductive material. This conductive material may be plated, deposited, injected or inserted by any other manner. In one arrangement a gold paste or silver paste is used. This conductive material completes the connection between the exposed surface of the underlying reference sensor 108 or nutrient sensor 110 within the perforation 118 and the graphene layer 116 of sections 120 on top of the polyimide layer 114. Any other manner, method or means of connecting the graphene layer 116 with the underlying reference sensor 108 or nutrient sensor 110 is hereby contemplated for use.

Ion Selective Membrane 122:

In the arrangement shown, as one example, an ion selective membrane 122 is applied to nutrient sensors 110 but not reference sensors 108. Ion selective membrane 122 is formed of any suitable size, shape and design and is configured to prevent all but select nutrients or ions to pass through the ion selective membrane 122. In this way, ion selective membrane 122 is what is known as a selectively permeable membrane in that it allows some materials, ions, nutrients, chemistries, molecules, constituents, etc. to pass through the ion selective membrane 122 while preventing other materials, ions, nutrients, chemistries, molecules, constituents, etc. from passing through the ion selective membrane 122.

In one or more arrangements, ion selective membrane 122 is formed of a PVC-based ion selective membrane that is selective to Ammonium, Calcium, Chlorine, Hydrogen, Nitrate, Magnesium, Phosphorus, Potassium, or Sodium ions or the like or any other materials, ions, nutrients, chemistries, molecules, constituents, or elements or range thereof or combination thereof.

In one or more arrangements, ion selective membrane 122 may be formed of PVC layer having a porous scaffold configuration on a molecular level. This may also be referred to as a nano-porous polymer membrane. In one or more arrangements, ion selective membrane 122 is what is known as an ionophore-doped membranes which may be used for functionalisation in ion sensing technologies such as ion-selective electrodes (ISEs). Doping the ion selective membrane 122 in this manner allows only selected ions through the porous ion selective membrane 122.

In the arrangement shown, as one example, where multiple nutrient sensors 110 are present on a cartridge 90, all of the nutrient sensors 110 may be configured to detect the same ion, which provides redundancy which may lead to higher accuracy and confidence in the reading. Alternatively, where multiple nutrient sensors 110 are present on a cartridge 90, each of the nutrient sensors 110 may be configured to detect a different ion, which provides the ability to sense the concentration of multiple nutrients using only a single cartridge 90. Another benefit of the cartridge and the co-located multiple nutrient sensors 110 is that the nutrient sensors 110 are able to detect various ion levels or nutrient levels at approximately the same position in the soil. This may be repeated by providing multiple cartridges 90 along the length of probe 14.

As one example, a single cartridge 90 having a reference sensor 108 and four nutrient sensors 110 may have an ion selective membrane 122 covering the first nutrient sensor 110 that is limited to hydrogen, an ion selective membrane 122 covering the second nutrient sensor 110 that is limited to Ammonium or Nitrate, an ion selective membrane 122 covering the third nutrient sensor 110 that is limited to Phosphorus, and an ion selective membrane 122 covering the first nutrient sensor 110 that is limited to Potassium, and in this way, a single cartridge 90 may be used to detect the pH, as well as the N, P, K concentrations of the soil.

In this example arrangement, the nutrient sensors 110 collect ion level readings that pass through the ion specific membranes 122 which prohibit other ions from passing through the ion specific membrane 122. These ion readings, nutrient readings, and/or fertility readings are then temperature compensated using the temperature reading from the temperature sensor assembly 28 and the raw data is transmitted in a data string with both Scaled Frequency Units (SFU) and temperature readings and moisture levels. In this example arrangement, this data is then stored and processed to equate parts per million (PPM) to pounds per acre (PPA) by moisture and temperature compensation along with normalization using information from reference sensor 108.

In the arrangement shown, as one example, a ceramic or Borosilicate glass membrane 124 is applied over reference sensor 108 and nutrient sensors 110.

In one arrangement, reference sensors 108 includes an ion selective membrane 122 similar to that identified above with respect to nutrient sensors 110. However, the ion selective membrane 122 applied to reference sensor 108 includes a silver/silver chloride ink or paste, which is very stable. This provides a reference reading or reference voltage or reference potential that the readings of the nutrient sensors 110 may be compared to.

Membrane 124:

In the arrangement shown, as one example, a membrane 124 is applied over reference sensor 108 and nutrient sensors 110. Membrane 124 is formed of any suitable size, shape and design and is configured to cover reference sensor 108 and nutrient sensors 110 so as to prevent soil particles, organic matter or other contaminants from adhering to the reference sensor 108 and nutrient sensors 110. In one arrangement, membrane 124 is formed of a ceramic or Borosilicate glass, however any other form of a material or a membrane is hereby contemplated for use that allows moisture, nutrients and the like to pass through the membrane 124 while preventing soil particles, organic matter or other contaminants from adhering to the reference sensor 108 and nutrient sensors 110.

Once cartridge 90 is formed, cartridge 90 is configured to be inserted within a receptacle 52 of probe 14.

Receptacle 52:

In the arrangement shown, as one example, probe 14 includes one or more receptacles 52. Receptacles 52 are formed of any suitable size, shape and design and are configured to receive a cartridge 90 therein with close and tight tolerances while facilitating an electrical connection of cartridge 90 with sensor PCB 176 and/or controller assembly 56, while forming a seal with cartridge 90 and while allowing the exterior surface 94 of cartridge 90 to engage the soil, among other features, objectives and advantages. Receptacles 52 are configured to hold a cartridge 90 therein during use. Receptacle 52 is configured to allow for the easy installation of cartridge 90 into receptacle. Receptacle is configured to allow for the easy removal of cartridge 90 from receptacle 52 after use and after cartridge 90 has exceeded its useful lifespan. This removable cartridge 90 feature allows the probe 14 to be reused by simply replacing the cartridges 90. This provides added emphasis on ensuring that the cartridges 90 are as low-cost as possible so as to ensure disposable cartridges 90 is economically feasible, which is something the system 10 and configuration presented herein accomplishes.

To facilitate this easy installation and removal of a cartridge 90, receptacle 52 and cartridge 90 are formed of complementary sizes and shapes. That is, in the arrangement shown, as one example, when cartridge 90 is generally rectangular in shape, receptacle 52 is similarly rectangular in shape and is sized and shaped to facilitate the easy mating insertion of cartridge 90 within receptacle 52. Any other shape is hereby contemplated for use for receptacle 52 as well as cartridge 90.

In the arrangement shown, as one example, receptacle 52 includes a sidewall 126 that extends inward from the exterior surface of probe 14 and connects to a rear wall 128. Rear wall 128 of receptacle 52 includes electrical contacts 112 therein that connect to the electrical contacts 106 in the interior surface 96 of cartridge 90. In the arrangement shown, electrical contacts 112 are electrically connected to electrical contacts 113 on an interior side of receptacle 52. In the arrangement shown, as one example, electrical contacts 113 connect with an edge connector 178 of sensor PCB 176 to facilitate communication of sensor measurements to controller assembly 56. Sensor PCB 176 is formed of any suitable size shape and design and is configured to communicate with controller assembly 56 and perform soil measurements with sensors 108 and 110. Alternatively, in some arrangements, electrical contacts 113 may be connected directly to controller assembly and sensor PCB 176 is omitted.

In the arrangement shown, electrical contacts 112 of receptacle 52 are compressible pogo pins compressible then contact electrical contacts 106 of cartridge 90 when cartridge 90 is inserted within receptacle 52. However, the opposite arrangement is hereby contemplated for use wherein the receptacle 52 includes the electrical contact pads that connect with pogo pins 106 of cartridge In the arrangement shown, as one example, when cartridge 90 is inserted within a receptacle 52, sealing member 104 engages and seals to the sidewall 126 of receptacle 52 thereby preventing moisture and contaminants from entering receptacle 52.

In one or more arrangements, a locking member 130 is associated with receptacle 52. Locking member 130 is formed of any suitable size, shape and design and is configured to lock cartridge 90 in receptacle 52 once installed. In one or more arrangements, locking member 130 may be formed of a screw or bolt or other fastener that extends through or engages cartridge 90 locks or tightens it to probe 14. In one or more arrangements, locking member 130 may be formed of a snap fit feature, a detent, a friction fit feature, a bracket, a pin, or any other component or system that secures or locks or helps to hold cartridge 90 into receptacle 52. This locking member 130 may also serve to ensure a good and strong seal between cartridge 90 and receptacle 52 so as to prevent moisture and contaminant infiltration.

In the arrangement shown, as one example, to help further prevent moisture and contaminant infiltration, a potting compound 174 is placed within receptacle 52. In one or more arrangements, potting compound 174 may be formed of any material that prevents or reduces the infiltration of water into receptacle 52 and/or behind cartridge 90. In one or more arrangements, potting compound 174 is a silicone, dielectric grease, glycerin grease, or any other compound that prevents or reduces the infiltration and effects of moisture.

Power Source 76:

In the arrangement shown, as one example, probe 14 includes a power source 76. Power source 76 is formed of any suitable size, shape and design and is configured to connect to and provide power for the electronic components of the probe 14. In one arrangement, power source 76 is formed of one or more batteries that are positioned inside tube 16 and/or head 22. In an alternative arrangement, power source 76 is positioned within an external telemetry unit 33 or another component that is connected to probe 14 by lead 54.

One of the benefits of having power source 76 positioned within the probe 14 is this makes probe 14 fully wireless. In this arrangement, probe 14 is inserted within the soil without any external components.

In an alternative arrangement, probe 14 may be connected by lead 54 to an external component such as gateway 32, telemetry unit 33 or the like.

Gateway 32 and Telemetry Unit 33:

In the arrangement shown, as one example, soil moisture and fertility sensor system 10 includes one or more gateways 32 and/or telemetry units 33. In one arrangement, gateway 32 and telemetry unit 33 are similar components with one difference being telemetry unit 33 is configured to connect directly to a probe 14 by way of lead 54 and in this way serve as an above-ground communication and control unit for probe 14. Note that a telemetry unit 33 is only used with a probe 14 when probe 14 does not have the components of telemetry unit 33 on board the probe 14 already. In contrast, gateway 32 is configured to serve as a base station that sends and receives wireless signals (or in some cases wired signals) between one or more probes 14 and/or telemetry units 33 installed throughout a farm or field. Notably, in one arrangement both a gateway 32 and telemetry unit 33 may serve as a repeater in a mesh network established between a plurality of probes 14 of the system 10, and as such, each probe 14, telemetry unit 33 and/or gateway 32 may serve as a repeater or essentially another gateway 32.

For purposes of avoiding redundancy both gateway 32 and telemetry unit 33 are both considered to have the following components and operate in a similar manner, unless specifically identified otherwise.

In the arrangement shown, as one example, gateways 32 and/or telemetry units 33 include a housing 132. Housing 132 is formed of any suitable size, shape and design and is configured and is configured to house and hold the components of gateways 32 and/or telemetry units 33 as is described herein. In the arrangement shown, as one example, housing 132 is formed of an enclosure having a main body 134 and a cover 136 that opens and closes and seals a hollow interior 138. In the arrangement shown, as one example, hollow interior 138 houses controller assembly 140.

Controller assembly 140 is formed of any suitable size, shape and design and is configured to control operation of some or all of the electronic components of gateway 32 and/or telemetry unit 33 and/or probe 14 if a probe 14 or multiple probes 14 are attached. In the arrangement shown, as one example, controller assembly 140 includes one or more processing circuits 142, memory 144, or one or more memory devices, and instructions 146, which may be in the form of software 148 or code 150, among multiple other components and systems.

In the arrangement shown, as one example, controller assembly 140 is electrically connected, either directly or indirectly, through wired connections, or wirelessly, to other electronic components of the system 10 including other gateways 32 and/or telemetry units 33 and probes 14. In the arrangement shown, as one example, controller assembly 140 includes stored instructions 146, such as operational routines, that controller assembly 140 executes. Alternatively and/or in addition, in the arrangement shown, as one example, controller assembly 140 receives information and/or instructions 146 from other gateways 32 and/or telemetry units 33, a user-controlled computing device 42, a cellular tower 34, the internet 36, the cloud 38, or another component of the system 10. Controller assembly 140 processes this information according to instructions 146 stored in memory 144 and then outputs commands thereby controlling operation of the controller assembly 140, any attached probes 14 or other components of the system 10.

In one or more arrangements, processing circuit 142 may be any computing device that receives and processes information and outputs commands according to instructions stored in memory 144. Memory 144 is any form of information storage such as flash memory, ram memory, a hard drive, or any other form of memory or combination thereof. Memory 144 may be included as a part of or operably connected to processing circuit 142. Controller assembly 140 may be a single component that is located at a single physical location. Alternatively, controller assembly 140 may be formed of multiple electronic components that are separated but electrically connected to one another that act in concert with one another.

Processing circuit 142 may be a single component that is located at a single physical location. Alternatively, processing circuit 142 may be formed of multiple electronic components that are separated but electrically connected to one another that act in concert with one another.

Memory 144 may be a single component that is located at a single physical location. Alternatively, memory 144 may be formed of multiple electronic components that are separated but electrically connected to one another that act in concert with one another.

Processing circuit 142 and memory 144 may be a single joined component that is located at a single physical location, such as within housing 132, or at any other location. Alternatively, processing circuit 142 and memory 144 may be formed of multiple electronic components that are separated but electrically connected to one another that act in concert with one another.

In one arrangement, controller assembly 140, which includes processing circuit 142, memory 144 and instructions 146, which may be in the form of software 148, code 150 or any other form of information, controls operation of and/or works in concert with any connected probes 14 and/or other gateways 32 and/or telemetry units 33. That is, in one arrangement, controller assembly 140 controls the operation of connected probes 14 and/or other gateways 32 and/or telemetry units 33 as well as the transmission of information through communication module 152, as is further described herein.

Communication module 152 is formed of any suitable size, shape and design and is configured to facilitate wireless communication of gateway 32 and/or telemetry unit 33 with other gateways 32 and/or telemetry units 33, cellular tower 34, the internet 36, the cloud 38, the farmer's or user's computing device 42 or any other component of the system 10.

In the arrangement shown, as one example, communication module 152 is any device or combination of devices that facilitate wireless communication of gateway 32 and/or telemetry unit 33. In the arrangement shown, as one example, communication module 152 includes an antenna 154 and radio 156 that facilitates wireless communication of gateway 32 and/or telemetry unit 33 and/or an attached probe 14 or other component of the system 10.

A receiver is used for radio 156 if one way communication is utilized in that a receiver is configured to transmit information only. In contrast, a transceiver is used for radio 156 if two-way communication is utilized in that a transceiver sends as well as receives information.

Communication module 152, including radio 156, is connected to an antenna 154. Antenna 154 is any device that facilitates the transmission and/or reception of the over-the-air signals, and may include a monopole antenna, dipole antenna, a loop antenna, a fractal antenna, or any other form of an antenna or combination thereof. Antenna 154 is configured to receive wireless signals from another component of the system 10, such as another gateway 32 and/or telemetry unit 33, computing device 42 or another component, transmits these signals to the receiver/transceiver of communication module 152, which processes these signals and then transmits these processed signals to processing circuit 142 which processes these signals according to instructions 146 stored in memory 144 as is further described herein.

Figure 6:
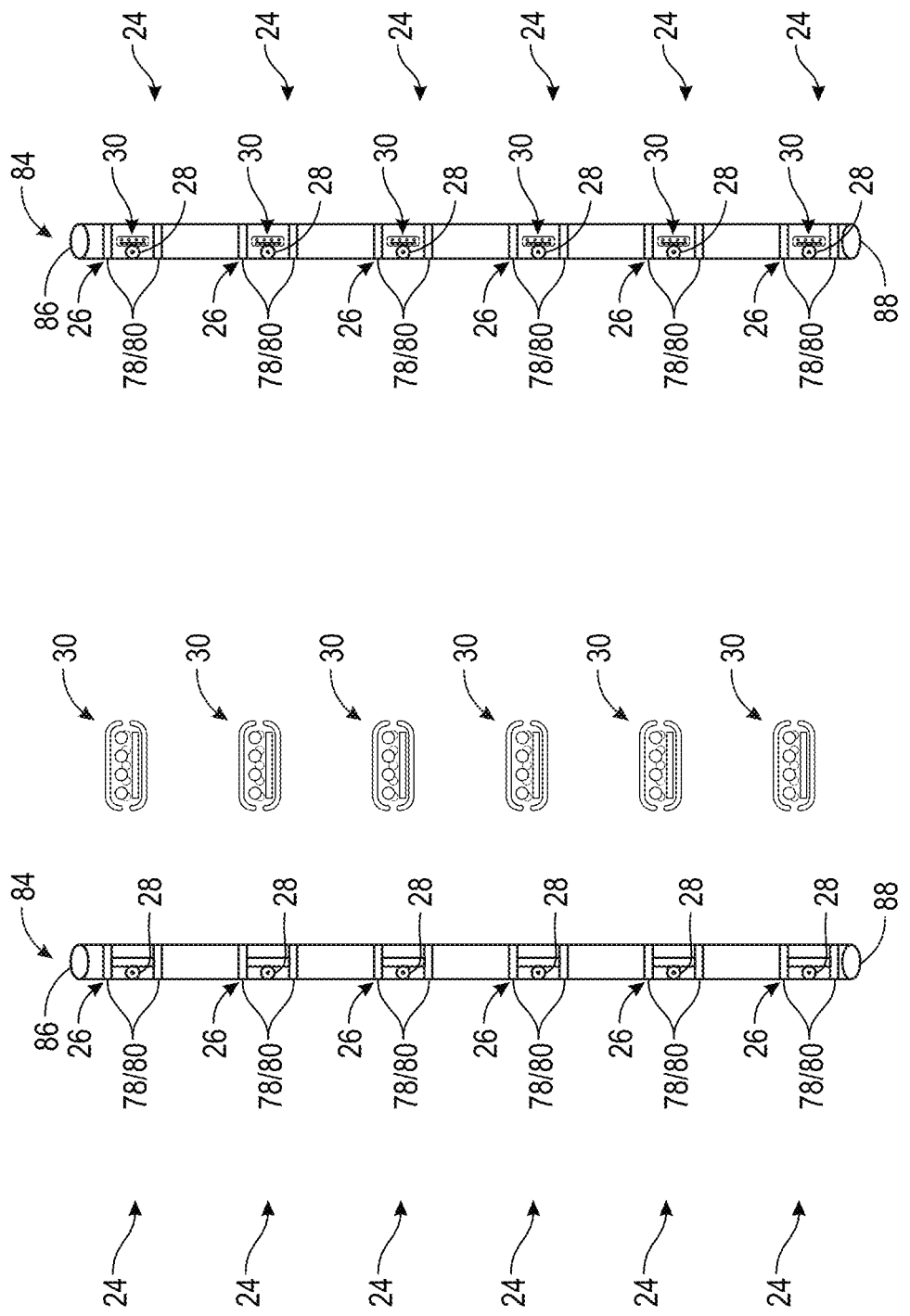
FIG. 6 shows tube segments of two probe for use in a soil moisture and fertility sensor system, in accordance with one or more embodiments; the view showing the tube with six sensor modules; the view showing a closeup of nutrition sensor assemblies of the sensor modules.
Figure 7:
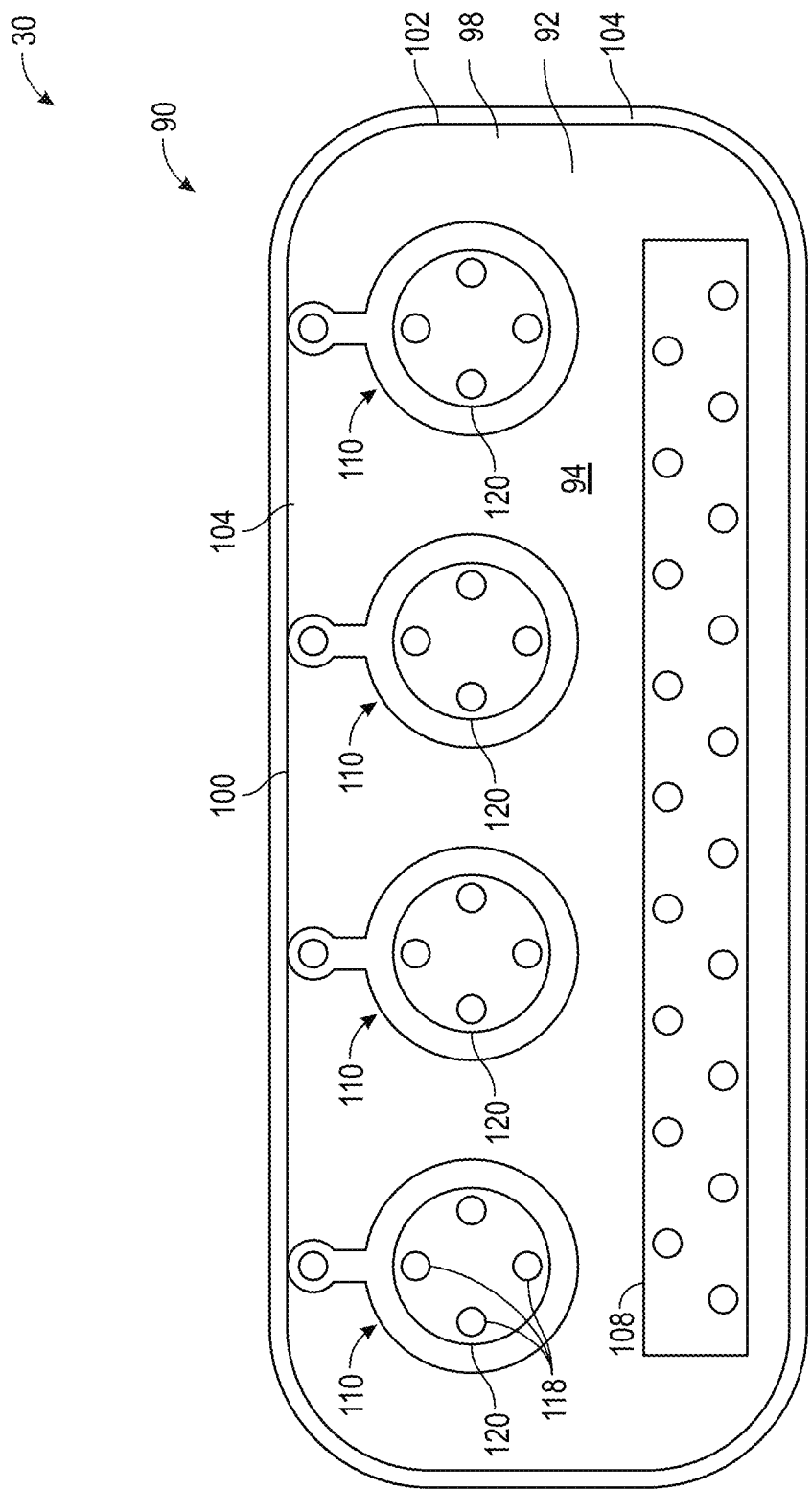
FIG. 7 shows a front view of a of nutrition sensor assembly, in accordance with one or more embodiments; the view showing the nutrition sensor assembly having four nutrition sensors and one reference sensor.
Figure 8:
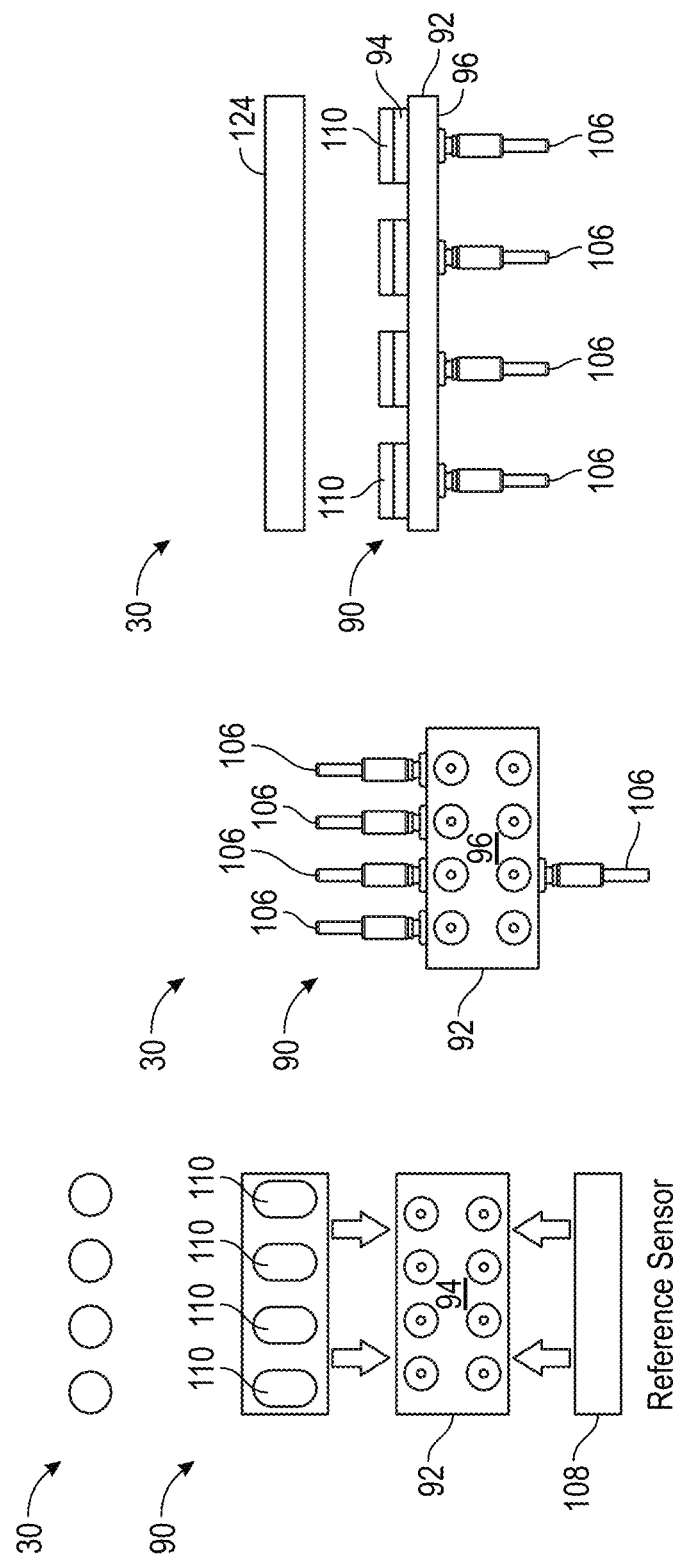
FIG. 8 shows front, rear, and side views of a nutrition sensor assembly, in accordance with one or more embodiments.
Figure 9:
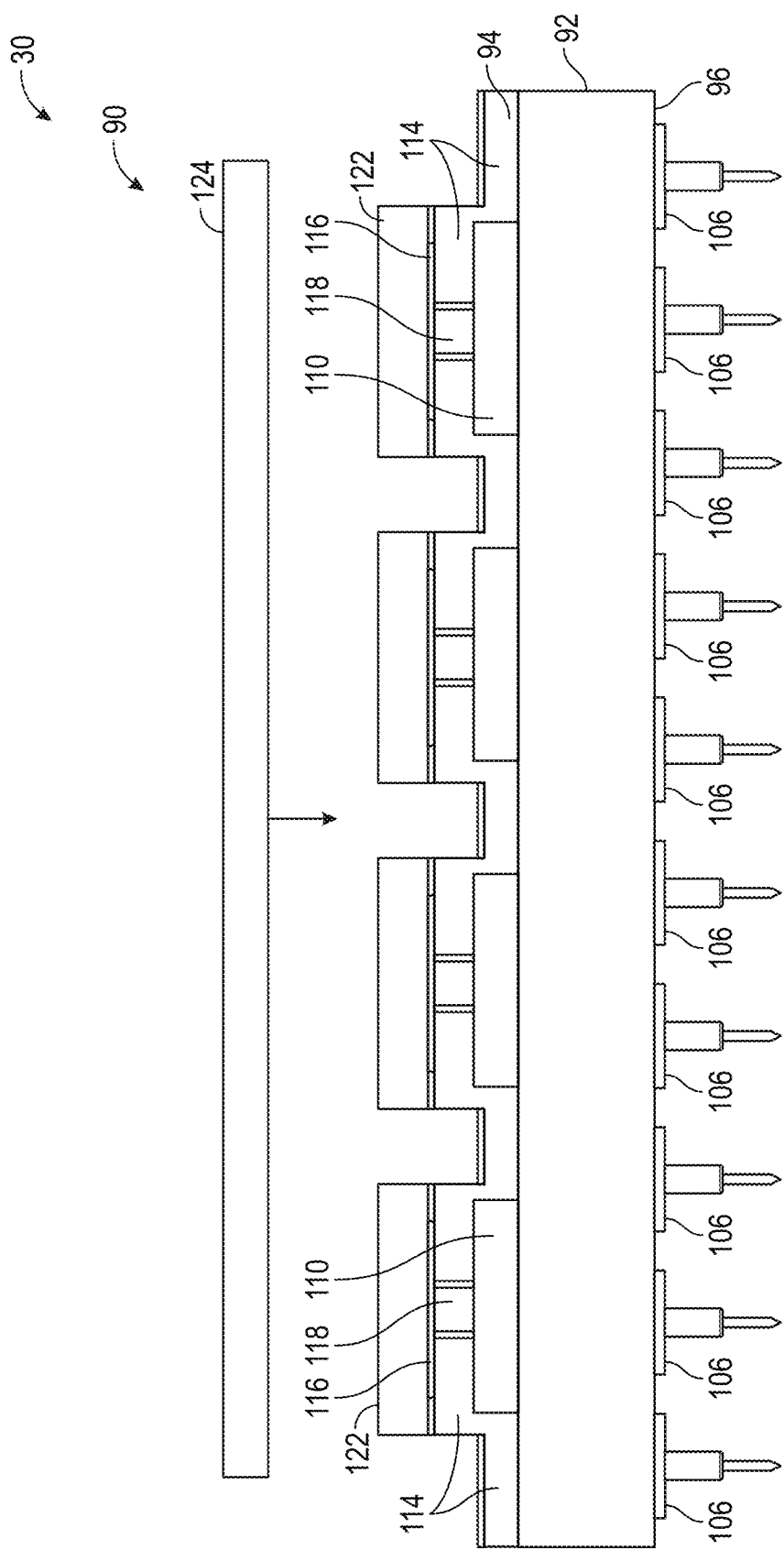
FIG. 9 shows a side view of a of nutrition sensor assembly, in accordance with one or more embodiments.
Figure 10:
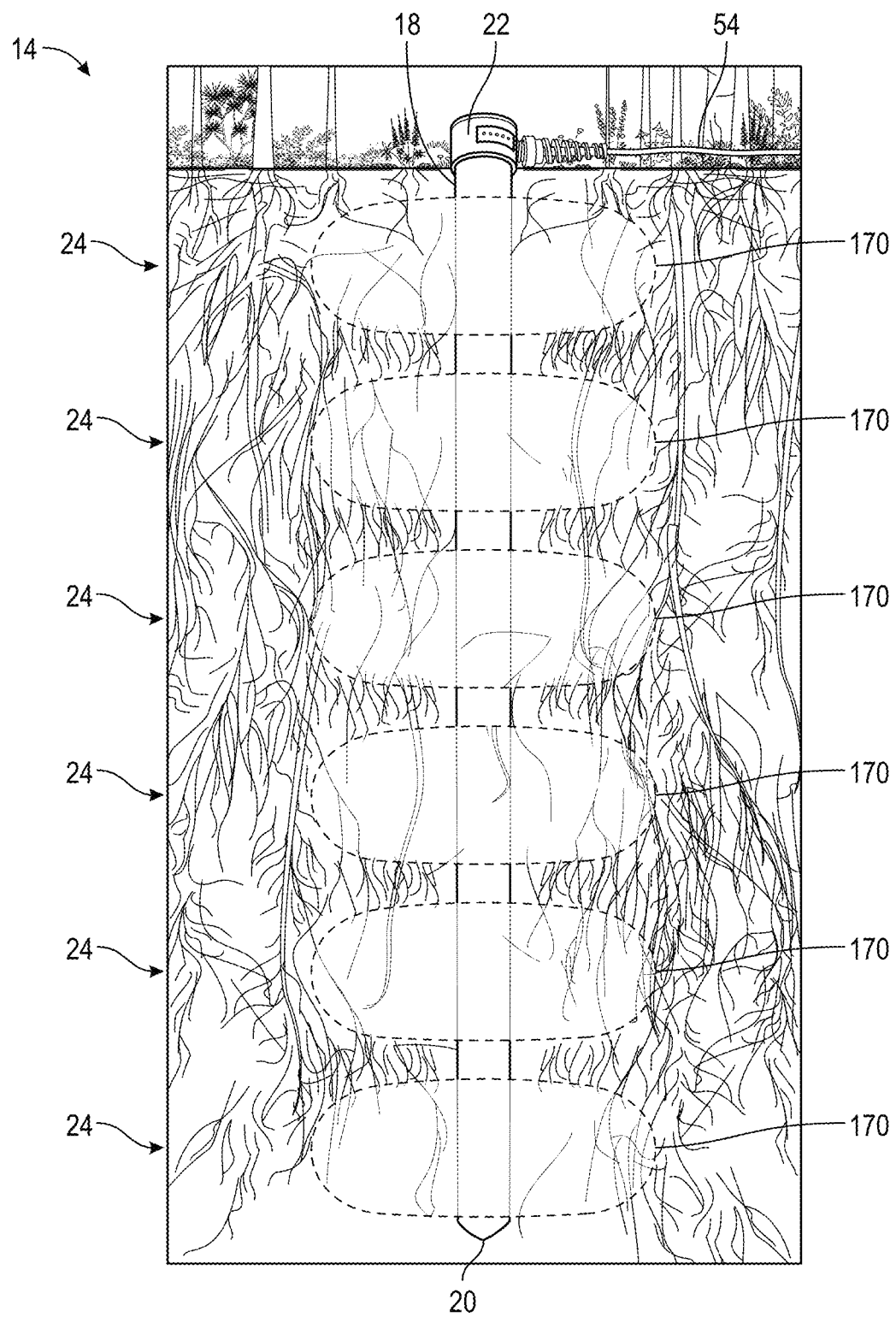
FIG. 10 shows a soil cross section of a wired probe positioned in the ground for testing soil moisture and fertility sensor system, in accordance with one or more embodiments; the view showing sensitivity ranges of a plurality of sensor modules positioned in the probe.
Figure 11:
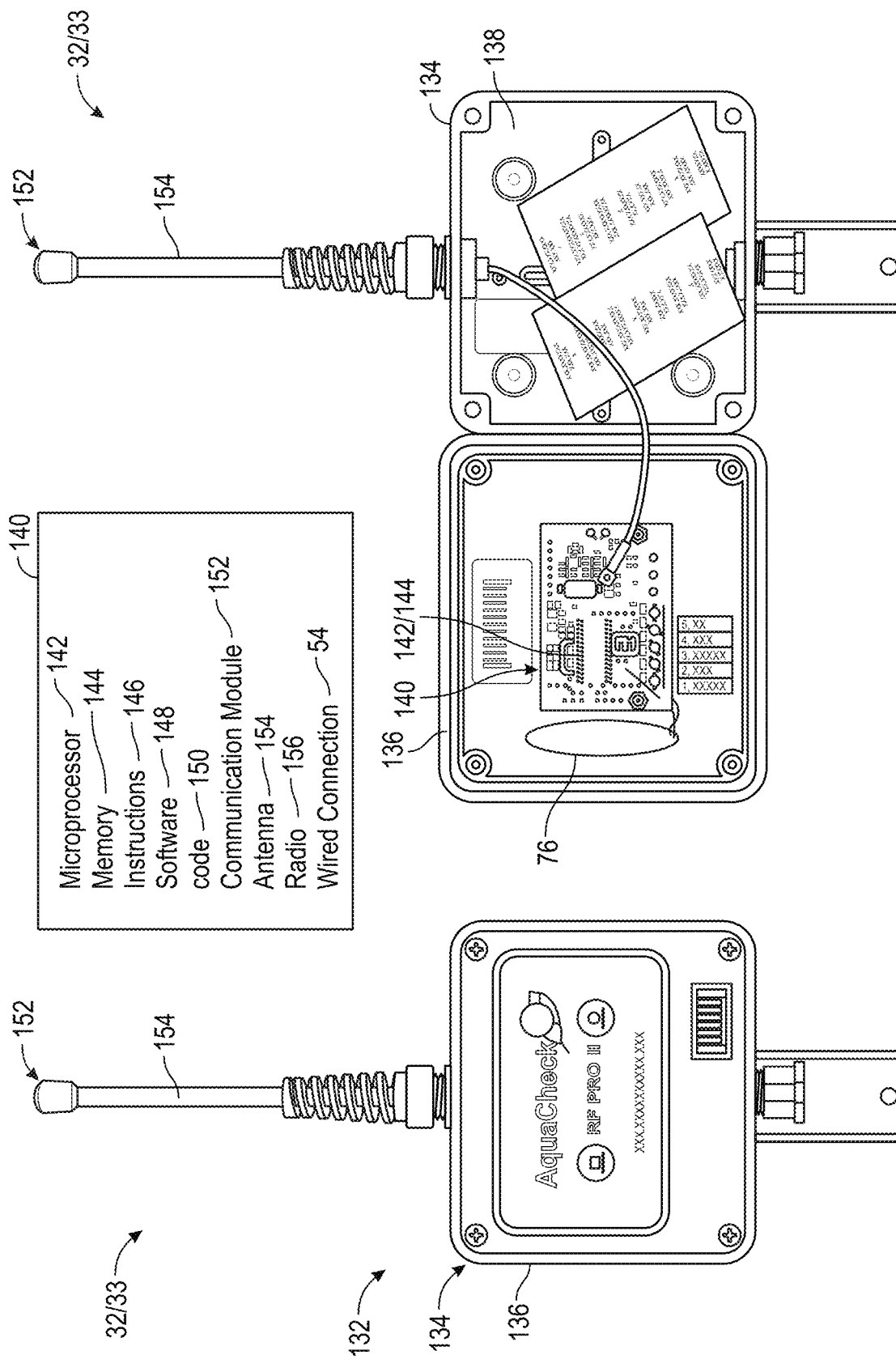
FIG. 11 shows views of a gateway for use in a soil moisture and fertility sensor system, in accordance with one or more embodiments; the left view showing a front exterior view of the gateway; the right view showing a front interior view of the gateway.
Figure 12:
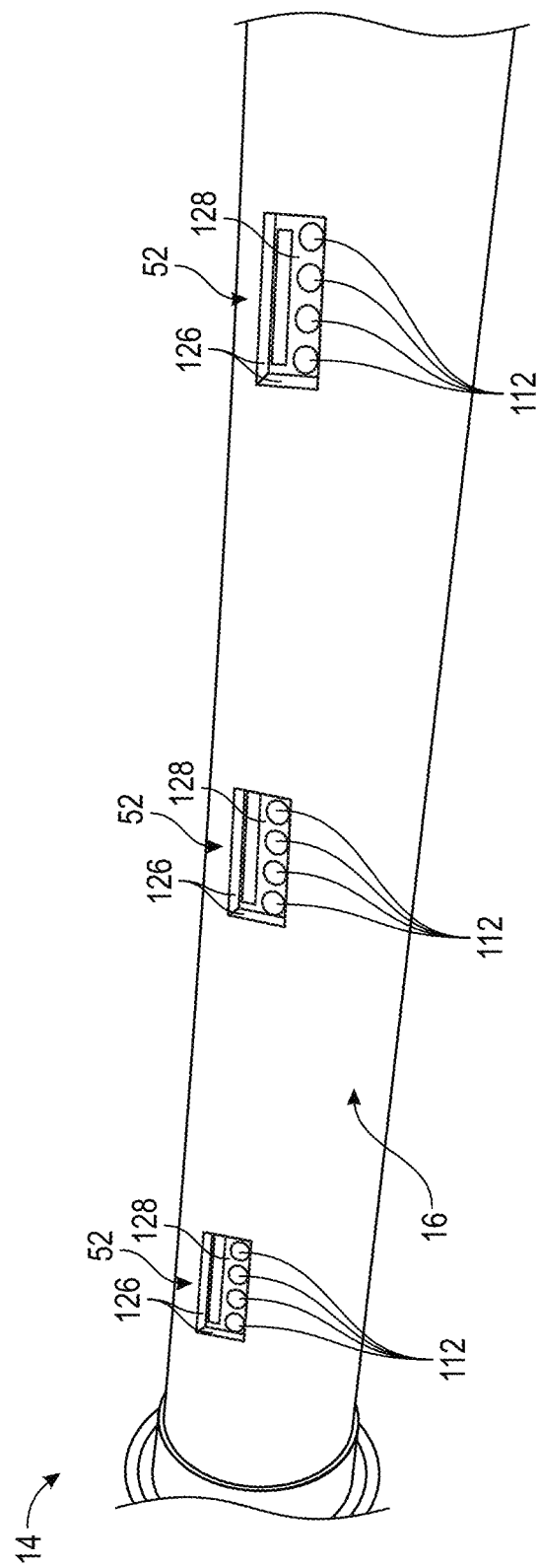
FIG. 12 shows a portion of a tube of a probe for use in a soil moisture and fertility sensor system, in accordance with one or more embodiments.
Figure 13:
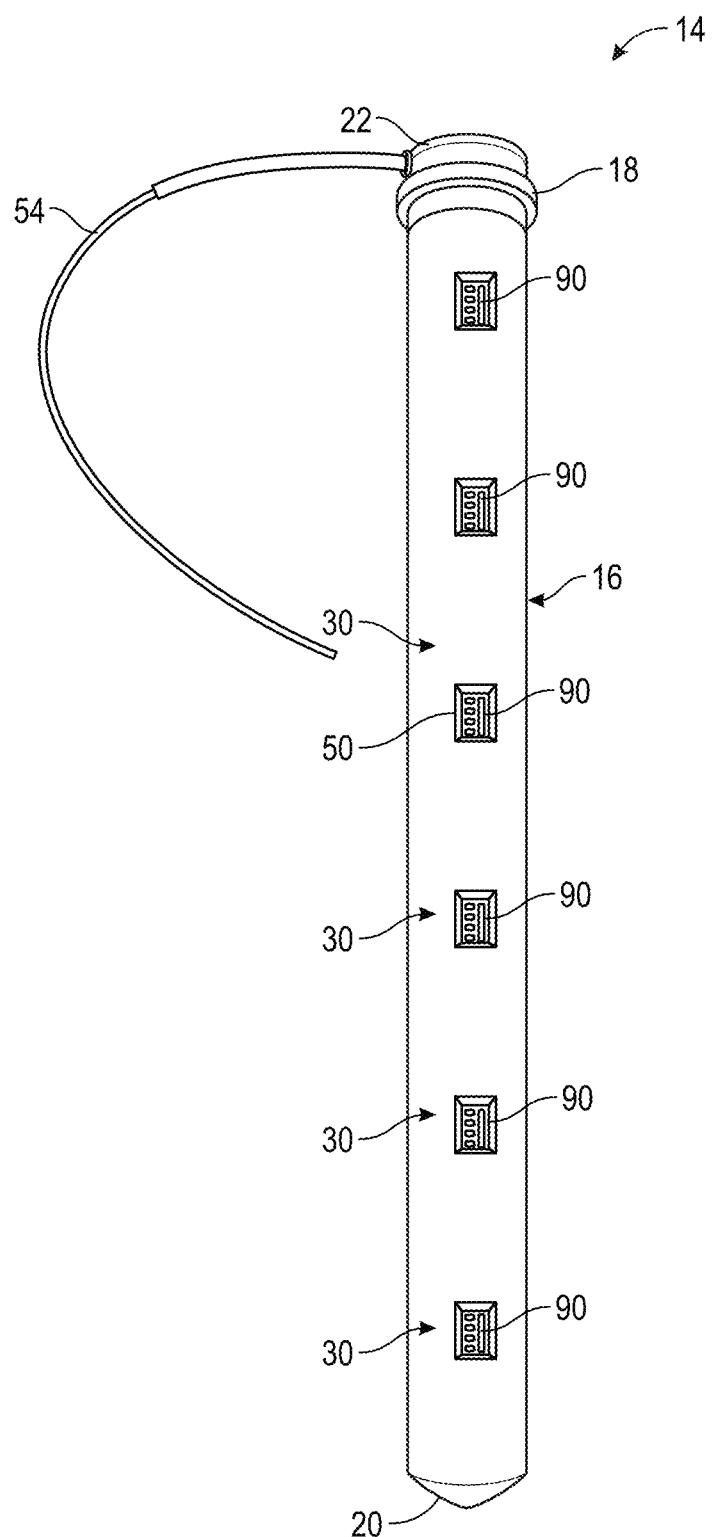
FIG. 13 shows a front view of a wired probe for use in a soil moisture and fertility sensor system, in accordance with one or more embodiments; the view showing the tube of the wired probe with six sensor modules.
Figure 14:
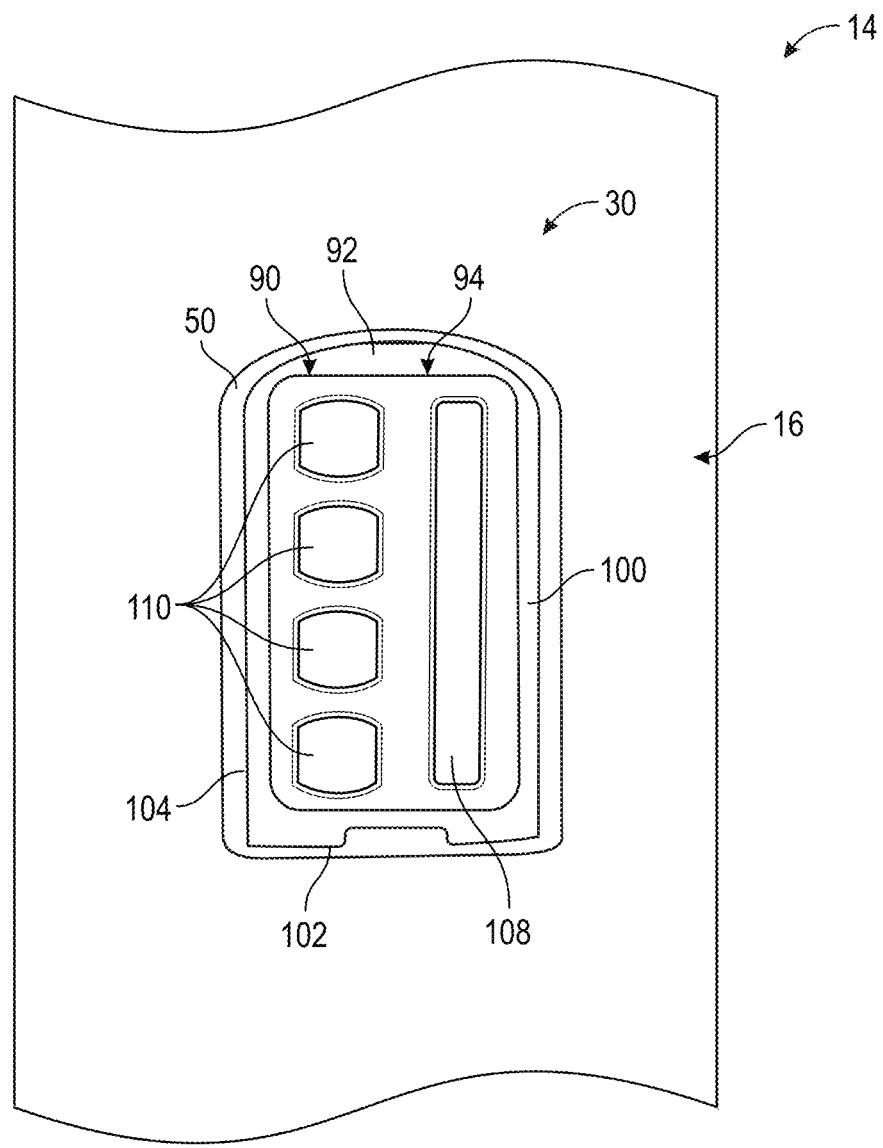
FIG. 14 shows a closeup view of a nutrition sensor assembly of a sensor module of the wired probe shown in FIG. 13, in accordance with one or more embodiments.
Figure 15:
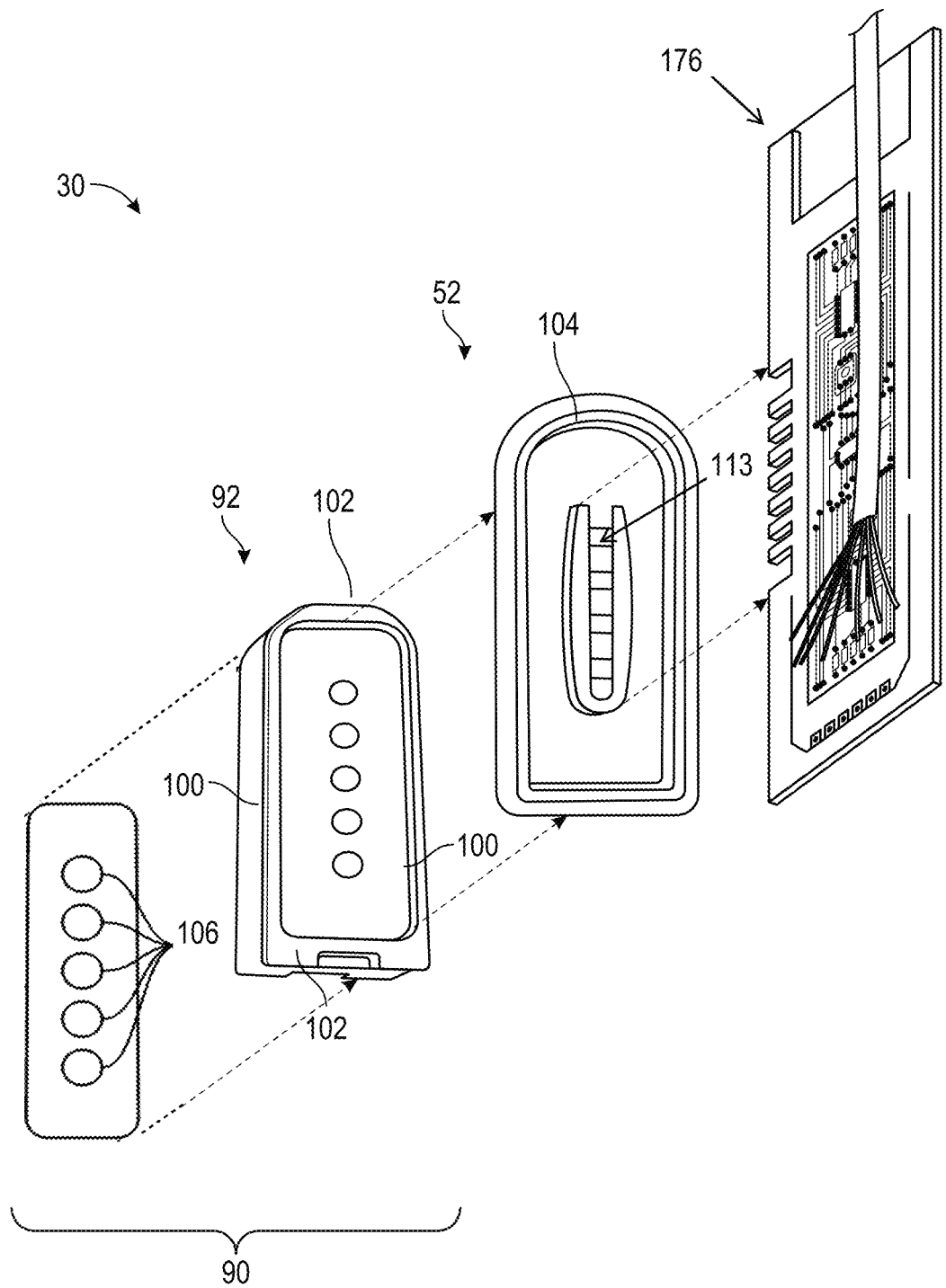
FIG. 15 shows an exploded lower rear left side perspective view of a nutrition sensor assembly of a sensor module of the wired probe shown in FIG. 13, in accordance with one or more embodiments; the view showing a sensor cartridge positioned for insertion into a receptacle; the view showing a sensor PCB positioned for connection to the receptacle.
Figure 16:
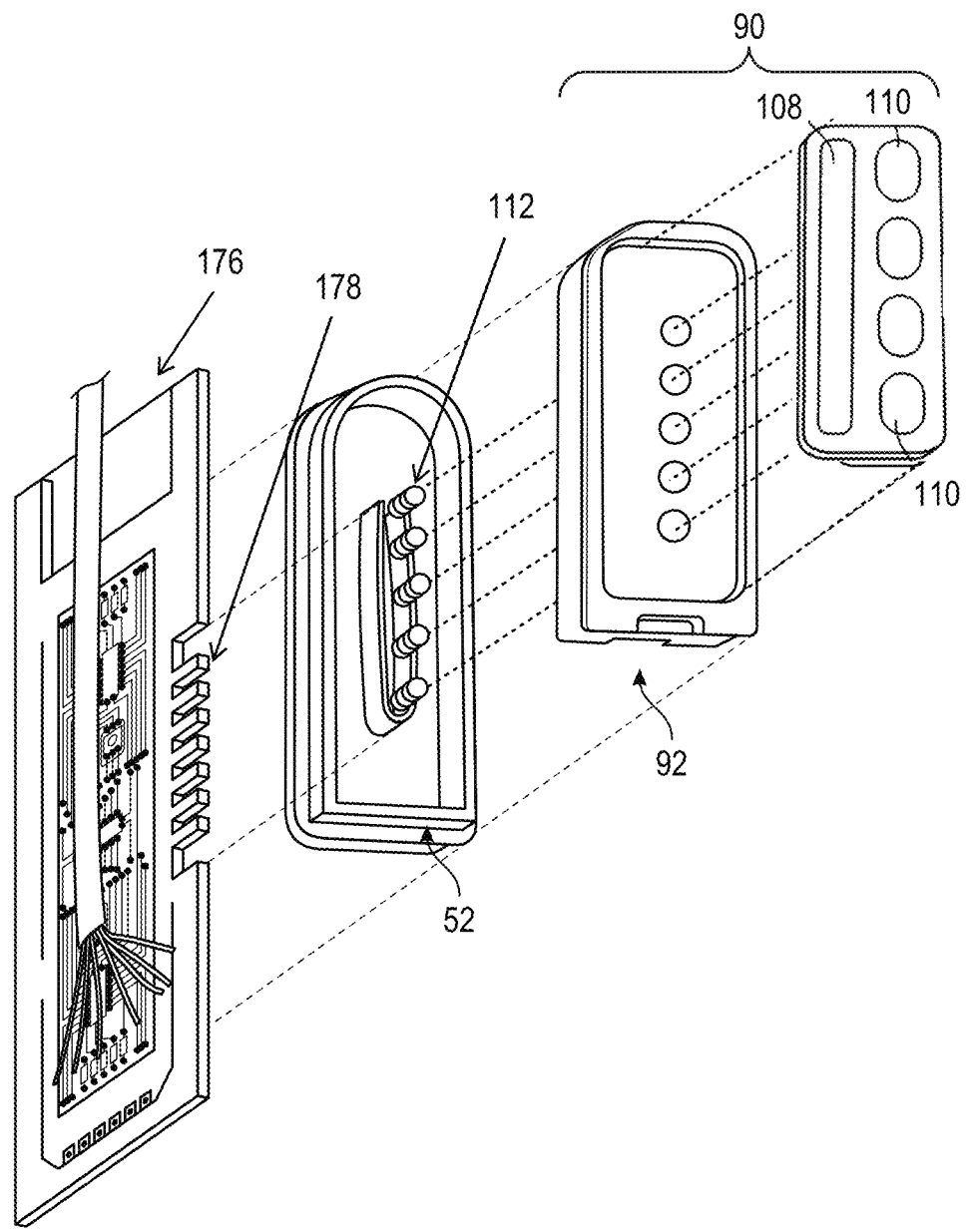
FIG. 16 shows an exploded lower front right side perspective view of a nutrition sensor assembly of a sensor module of the wired probe shown in FIG. 13, in accordance with one or more embodiments; the view showing a sensor cartridge positioned for insertion into a receptacle; the view showing a sensor PCB positioned for connection to the receptacle.

Communication and Calculations:

In the arrangement shown, as one example, a plurality of probes 14 are installed across a field or farm. Each of the probes 14 periodically and/or according to a plan, prescription, schedule or other program or a user initiated request, makes a moisture measurement using moisture sensor assemblies 26, a temperature measurement using temperature sensor assemblies 28 and a fertility measurement using fertility sensor assemblies 30 at the location of each sensor modules 24. Note, however, that not all sensor modules 24 include a fertility sensor assembly 30. In contrast, with reference to FIG. 6, insert 84 only includes a fertility sensor assembly 30 as part of the top three sensor modules 24. This is because fertility and/or nutrients are primarily concentrated in the upper regions of the soil. Or, farmers are only interested in knowing the fertility and/or nutrient concentrations in the upper regions of the soil.

In the arrangement shown, as one example, each of the plurality of probes 14 include an on-board communication module 70 or are connected by lead 54 to a telemetry unit 33 or gateway 32. In one arrangement, as one example, probe 14 makes a moisture measurement using moisture sensor assemblies 26, a temperature measurement using temperature sensor assemblies 28 and a fertility measurement using fertility sensor assemblies 30 at the location of each sensor modules 24 (collectively a measurement). These measurements are transmitted by wireless communication through communication module 70 of probe 14 or communication module 152 of telemetry unit 33. In one arrangement, a plurality of measurements are stored in memory 62/144 and transmitted in bulk so as to save power and reduce the number of data transmissions. This process of collecting readings, which are saved for future communications, is commonly referred to as EDA (Environmental Data Acquisition). This data is then converted to a communications protocol that is used to transmit the data wirelessly when desired.

These wireless signals are then received by a generally centrally positioned gateway 32 which then re-transmits them to cellular tower 34, or another communication installation or system. Cellular tower 34 then transmits the information through one or more information networks 158, which may be a wireless network, a wired network, or any combination thereof, to the internet 36 and/or the cloud 38. In one or more arrangements, these measurements are stored in database 40.

One of the benefits of system 10 is that the co-location of moisture sensor assemblies 26, temperature sensor assemblies 28 and fertility sensor assemblies 30 at the location of each sensor modules 24 allows for normalization of readings from moisture sensor assemblies 26, a fertility sensor assemblies 30 at the location of each sensor modules 24 as temperature has an effect on moisture level readings from moisture sensor assemblies 26 and moisture and temperature have effect on readings from fertility sensor assemblies 30. In addition, readings from reference sensor 108 are used to normalize readings from ion specific nutrient sensors 110 having ion selective membranes 122 thereon. Using an algorithm or other program, this normalization may occur at the on-board controller assembly 56, or connected controller assembly 140 of a connected gateway 32 or telemetry unit 33, or alternatively the raw data may be transmitted to database 40 and the normalization or calculations may occur in association with database 40.

To facilitate this data processing, in the arrangement shown, as one example, database 40 includes or is connected to or is associated with a processing circuit 160, memory 162, or one or more memory devices, and instructions 164, which may be in the form of software or code or algorithms, among other components and systems. Alternatively and/or in addition to processing circuit 160, memory 162, and/or instructions 164 being associated with database 40, processing circuit 160, memory 162, and/or instructions 164 may be associated with computing device 42, or alternatively processing circuit 160, memory 162, and/or instructions 164 may be associated with both database and computing device 42 which operate in a cooperative manner with one another.

To avoid redundancy, processing circuit 160, memory 162, and instructions 164, whether associated with database 40 or computing device 42, are similar to that described herein with respect to probe 14, gateway 32 and/or telemetry unit 33. In this arrangement, processing circuit 160 in association with memory 162 and instructions 164 performs calculations to convert the raw readings from probes 14 to normalized readings which may be in the form of parts per million (PPM) or pounds per acre (PPA) or any other format that is useful and valuable to the farmer.

In one or more arrangements, processing circuit 160, memory 162, and instructions 164 of database 40 and/or computing device 42 may be configured to additionally or alternatively perform various data analytics processes on data stored in database 40 to derive additional data metrics pertinent to assessment of soil measurements. In some arrangements, the data analytics processes may correlate data in database 40 with data in third party data sources to derive such data metrics. As an illustrative example, in one or more arrangements the data analytics processes may cross correlate data in database with publicly available data sets (e.g., provided by various government agencies), which monitor temperature, ground water, and/or weather, for example, to derive additional data metrics. In one or more embodiments, the analytics processes may be configured to analyze the data and learn, over time, identify trends or various conditions of concern. Additionally or alternatively, analytics processes may be configured to analyze the data and learn over time predictive models, for example, to predict future soil conditions that will result from a proposed soil treatment based on based on current measurements. Such learning by the analytics processes may include, for example, generation and refinement of classifiers and/or state machines configured to map input data values to such trends or conditions of concern. In various embodiments, analysis by the analytics processes may include various guided and/or unguided artificial intelligence and/or machine learning techniques including, but not limited to: neural networks, genetic algorithms, support vector machines, k-means, kernel regression, discriminant analysis and/or various combinations thereof. In different implementations, analysis may be performed locally, remotely, or a combination thereof.

In association with and/or in addition to performing the normalization operation converting raw data to normalized and useful data and/or analytics processes, in one arrangement database 40 and/or computing device 42 communicatively connected to database 40 generates displays 44 of the measurement information from probes 14. These displays 44 may be any form of presentation of the information or measurements generated by probes 14. This may include charts, graphs, diagrams, tables, spreadsheets, or the like. These displays 44 may be integrated with or overlaid on or otherwise associated with other forms of information such as yield maps, application maps, seeding maps, treatment maps, spraying maps, or any other form of information that provides greater information and insight to the farmer. These displays 44 may be interactive and may be manipulated by the farmer or a crop-insight manager or agronomist or the like in any way to yield practically any form of insight into field health.

In the arrangement shown, as one example, these displays 44 are displayed on the interactive display 168 of computing device 42 which may take the form of a desktop or laptop computer, a smart phone, a tablet or any other form of a computing device. Computing device 42 is then used by the farmer or a crop-insight manager or agronomist or the like to provide actionable insights.

In response to the insights provided by the information provided by probes 14, analytics processes, and/or displays 166, the farmer then may take action by amending the inputs 46. If the land is irrigated, the farmer may amend the amount of water 48 applied to the field. Alternatively, the farmer may amend the nutrients 50 applied to the field.

One of the benefits of the system 10 is that probes 14 may provide multiple nutrient-specific measurements at multiple depths through the use of fertility sensor assemblies 30 having multiple nutrient sensors 110 each having an ion selective membrane 122 is that the farmer may specifically address nutrient deficiencies. That is, if the field is low in potassium, the farmer may apply only potassium; if the field is low in nitrogen, the farmer may apply only nitrogen; and so on. As such, for the first time, the farmer may in real-time have access to moisture and specific nutrient information across a farm or field. With nutrient specific information the farmer may specifically address deficiencies. This reduces cost by eliminating the use of unneeded nutrients. This also improves the environment as this reduces the potential for nutrient runoff and offsite contamination.

Simultaneous Operation-Individual Operation:

In the arrangement shown, as one example, probes 14 include multiple sensor modules 24 each having a moisture sensor assembly 26 and a temperature sensor assembly 28 and some of them having a fertility sensor assembly 30 which may include a reference sensor 108 as well as multiple nutrient sensors 110. In one arrangement, when a measurement is taken, all of the measurements are taken simultaneously. That is, all of the sensors of sensor modules 24 are operated at the same time. That is each of the moisture sensor assemblies 26 and the temperature sensor assemblies 28 and the reference sensor 108 as well as multiple nutrient sensors 110 of the fertility sensor assemblies 30 are energized and take a measurement at the same time or approximately at the same time. This arrangement may provide some benefits such speed and being able to perform a complete measurement within a minimum amount of time. Another benefit may be minimal battery usage.

However, performing multiple measurements simultaneously provides some risks and drawbacks. Namely, the energization of multiple sensors located close to one another may cause interference that skews or obfuscates the readings.

In an alternative arrangement, multiple sensors are operated at different times. In one arrangement, all of the moisture sensor assemblies 26 are operated at the same time while the temperature sensor assemblies 28 and fertility sensor assemblies 30 are not energized. This arrangement makes the moisture measurement at all sensor modules 24 at the same time.

In one arrangement, all of the temperature sensor assemblies 28 are operated at the same time while the moisture sensor assemblies 26 and fertility sensor assemblies 30 are not energized. This arrangement makes the temperature measurement at all sensor modules 24 at the same time.

In one arrangement, all of the fertility sensor assemblies 30 are operated at the same time while the moisture sensor assemblies 26 and temperature sensor assemblies 28 are not energized. This arrangement makes all the fertility measurements at all sensor modules 24 at the same time.

As an alternative to this arrangement, as fertility sensor assemblies 30 include a reference sensor 108 and multiple nutrient sensors 110, in one arrangement, only one of the reference sensor 108 and multiple nutrient sensors 110 of each fertility sensor assembly 30 is operated at the same time while the others of the reference sensor 108 and multiple nutrient sensors 110 of each fertility sensor assembly 30 are not energized. This way, at any one time, only one of the reference sensors 108 and multiple nutrient sensors 110 of each fertility sensor assembly 30 is energized.

In an alternative arrangement, only one of the multiple sensor modules 24 are energized at any one time. In one arrangement, as one example, if a probe 14 includes three sensor modules 24, each having a moisture sensor assembly 26, a temperature sensor assembly 28 and a fertility sensor assembly 30 having a reference sensor 108 and multiple nutrient sensors 110, the measurement is performed in the following manner:

All of the sensors of the first sensor module 24 are energized simultaneously;
All of the sensors of the second sensor module 24 are energized simultaneously;
All of the sensors of the third sensor module 24 are energized simultaneously.

In this way, all of the measurements are performed in a manner wherein the operation of one sensor module 24 does not affect the other sensor modules 24. However, the simultaneous energization of the sensors within each sensor module 24 may affect the readings of the other sensors within each sensor module 24.

In another arrangement, as one example, if a probe 14 includes three sensor modules 24, each having a moisture sensor assembly 26, a temperature sensor assembly 28, and a fertility sensor assembly 30 having a reference sensor 108 and multiple nutrient sensors 110, only one of the moisture sensor assembly 26, temperature sensor assembly 28, and fertility sensor assembly 30 of one of the sensor modules 24 is energized and/or read at any one time. As an example, the measurement is performed in the following manner:

The first sensor module 24 is measured in the following manner:
The moisture sensor assembly 26 is energized and read;
The temperature sensor assembly 28 is energized and read;

The reference sensor 108 and multiple nutrient sensors 110 of the fertility sensor assembly 30 are read simultaneously or nearly simultaneously;

The second sensor module 24 is measured in the following manner:
  The moisture sensor assembly 26 is energized and read;
  The temperature sensor assembly 28 is energized and read;
  The reference sensor 108 and multiple nutrient sensors 110 of the fertility sensor assembly 30 are read simultaneously or nearly simultaneously; and The third sensor module 24 is measured in the following manner:
  The moisture sensor assembly 26 is energized;
  The temperature sensor assembly 28 is energized; and
  The reference sensor 108 and multiple nutrient sensors 110 of the fertility sensor assembly 30 are energized simultaneously.

In this way, all of the measurements are performed in a manner wherein the operation of one sensor module 24 does not affect the other sensor modules 24. In addition, the operation of the moisture sensor assembly 26, temperature sensor assembly 28 and fertility sensor assembly 30 does not affect the other of the moisture sensor assembly 26, temperature sensor assembly 28 and fertility sensor assembly 30 within each sensor module 24. However, the simultaneous energization of the reference sensor 108 and multiple nutrient sensors 110 of each fertility sensor assembly 30 may affect the readings of the other sensors within the fertility sensor assembly 30.

In another arrangement, as one example, if a probe 14 includes three sensor modules 24, each having a moisture sensor assembly 26, a temperature sensor assembly 28 and a fertility sensor assembly 30 having a reference sensor 108 and multiple nutrient sensors 110 only one of the moisture sensor assembly 26, temperature sensor assembly 28 and fertility sensor assembly 30 of one of the sensor modules 24 is energized at any one time with each of the reference sensor 108 and multiple nutrient sensors 110 of the fertility sensor assembly 30 energized individually. As an example, the measurement is performed in the following manner:

The first sensor module 24 is measured in the following manner:
  The moisture sensor assembly 26 is energized and read;
  The temperature sensor assembly 28 is energized and read;
  The reference sensor 108 of fertility sensor assembly 30 is read;
  Each of the multiple nutrient sensors 110 of fertility sensor assembly 30 are individually read sequentially;

The second sensor module 24 is measured in the following manner:
  The moisture sensor assembly 26 is energized and read;
  The temperature sensor assembly 28 is energized and read;
  The reference sensor 108 of fertility sensor assembly 30 is read;
  Each of the multiple nutrient sensors 110 of fertility sensor assembly 30 are individually read sequentially; and The third sensor module 24 is measured in the following manner:
  The moisture sensor assembly 26 is energized and read;
  The temperature sensor assembly 28 is energized and read;
  The reference sensor 108 of fertility sensor assembly 30 is read; and
  Each of the multiple nutrient sensors 110 of fertility sensor assembly 30 are individually read sequentially.

In this way, all of the measurements are performed in a manner wherein the operation of any sensor of any sensor module 24 does not affect any other measurement of any other sensor modules 24. This is perhaps the most cautious manner of operating the probe 14. However, this manner of operation takes the longest and may increase power draw as functional components of the probe 14 are operating for a longer period of time as opposed to going into a sleep mode between periodic measurements.

Any other manner of operation of probe 14 is hereby contemplated for use.

Assembly and Installation:

In the arrangement shown, as one example, soil moisture and fertility sensor system 10 is assembled and installed in the following manner: Cartridges 90 having the desired ion selective membranes 122 are installed into each of the receptacles 52 along the length of tube 16 of probe 14. This installation is accomplished by inserting a cartridge 90 into each receptacle 52 by aligning the peripheral edge 98 of cartridge 90 with the walls of receptacle 52 and pressing the cartridge 90 into the receptacle 52 until the electrical contacts 106 of cartridge 90 engage and electrically connect to the electrical contacts 112 of receptacle 52. In this position, the exterior surface of cartridge 90 or more specifically the exterior surface of reference sensor 108 and/or nutrient sensors 110 are in approximate flush alignment with the exterior surface of tube 16 of probe 14.

Alternatively, it is also contemplated that, in one or more arrangements, the exterior surface of cartridges 90 may be slightly recessed to or slightly proud of the exterior surface of tube 16. However, cartridges 90 are configured to operate through direct connection with the soil. As such, while recessing the exterior surface of cartridges 90 provides some protection to scratching and damaging cartridge 90 upon insertion of the probe into the soil, this recessing poses problems when it comes to ensuring a direct connection between the soil and the exterior surface of the cartridges 90. In contrast, having the exterior surface of cartridges 90 protrude slightly from the exterior surface of the tube 16 helps to ensure a direct connection with the soil. However, having the exterior surface of the cartridges 90 protrude from the exterior surface of the tube 16 exposes the thin and delicate membranes on the surface of the reference sensor 108 and nutrient sensors 110 to damage during insertion of the probe 14 into the soil.

In one arrangement, to facilitate installation of probe 14 into the soil of a field, first the location is selected. Second a hole is formed by suitable measures in the soil of the field. In one arrangement, care is taken when forming the hole that the sides of the hole have as crisp an edge as possible so as to ensure the best possible direct engagement between the soil and the cartridges 90 of probe 14. As examples, this hole may be formed by cutting, plugging, drilling or any other manner, method or means.

Once the hole is formed, the probe 14 is carefully inserted within the hole until the fully inserted. Once probe 14 is inserted into the soil, in one arrangement, as one example, to help ensure direct contact between cartridges 90 the soil, a slurry is formed in the soil around the probe 14 and/or the soil is emulsified around the probe 14 thereby ensuring the soil makes direct contact with the cartridges 90. In some arrangements, slurry may be formed by mixing a specified ratio of soil with water. This will ensure a consistent slurry is used for all sensors.

However, injecting a slurry or emulsifying the soil affects the moisture content of the soil around the probe 14 which affects the moisture readings for some time after installation until the soil around the probe 14 re-establishes equilibrium with the surrounding soil. Typically, such equilibrium occurs within a few days.

Once probe 14 is inserted, the sensor modules 24 measure the characteristics of the soil in areas 170 around the sensor modules 24. Each sensor module 24 provides information regarding the characteristics of the soil at different depths, including moisture level, temperature, and the concentration of nutrients.

After the useful life of the cartridges 90 has been exceeded, which in one arrangement is the length of a growing season which may be as long as nine-months, probe 14 is removed from the soil and the cartridges 90 are removed from each receptacle 52. New cartridges 90 are inserted into each receptacle 52 and the probe 14 is ready to be used again.

Biasing Member 172:

As mentioned herein, reference sensor 108 and nutrient sensors 110 are formed of what are known as direct contact ion sensors which operate through the direct contact of the soil with the sensors. As such, it is important to ensure that direct contact between the soil and reference sensor 108 and nutrient sensors 110 is established. In one arrangement, to ensure this direct contact occurs, probe 14 includes a biasing member 172. Biasing member 172 is formed of any suitable size, shape and design and is configured to selectively force cartridges 90 outward from tube 16 after tube 16 is inserted within the soil.

In this arrangement, cartridges 90 may be recessed to the exterior surface of tube 16 during installation of the tube 16 into the soil. Then, after installation, biasing member 172 is engaged or operated which forces cartridges 90 outward until the exterior surface of cartridges 90 engage the soil in flat and flush and constant and repeatable and reproducible engagement. This insures accurate and consistent readings between sensor modules 24 and between probes 14. This also eases the installation process and eliminates the need to inject a slurry around the probe 14 or emulsify the soil around the probe 14.

In one arrangement, biasing member 172 is a spring loaded system that once engaged applies a spring loaded force thereby forcing cartridges 90 outward until they engage the soil. In another arrangement, biasing member 172 is a mechanical cam system that when engaged includes an arm that forces cartridges 90 outward until they engage the soil. In another arrangement, biasing member 172 includes one or more electro mechanical devices, such as solenoids, that when engaged drive cartridges 90 outward until they engage the soil. Any other arrangement or configuration or system is hereby contemplated for use as biasing member 172.

Alternative Graphene and/or Carbon Layers:

In the arrangement described herein, graphene layer 116 is formed by applying a laser to the polyimide layer 114. However, any other manner, method or means of forming and/or connecting graphene layer 116 to the underlying reference sensor 108 or nutrient sensor 110 is hereby contemplated for use.

As one example, as an alternative, graphene flakes are overlaid on the exterior facing surface of reference sensor 108 or nutrient sensor 110 which are treated with an adhesive, which in one arrangement is an acrylic adhesive. Then pressure is applied to ensure a tight fit and secure attachment between the graphene flakes of the graphene layer 116 and the underlying reference sensor 108 or nutrient sensor 110. This may provide a more-conductive graphene layer 116 and a more-stable manufacturing process.

As another example, as another alternative, graphene flakes are overlaid on the exterior facing surface of reference sensor 108 or nutrient sensor 110. Then a laser, which in one arrangement is a CO2 laser is applied over some or all of the area covered by the graphene flakes. In doing so, a portion of the material of the reference sensor 108 or nutrient sensor 110 are melted and/or mixed, and/or fused and/or welded together with the graphene flakes of graphene layer 116 thereby securely affixing the graphene layer 116 to the underlying reference sensor 108 or nutrient sensor 110. This may provide a more-conductive graphene layer 116 and a more-stable manufacturing process.

These manufacturing processes may be less prone to oxidation. Since reference sensor 108 and nutrient sensor 110 operate at very low voltage, in the range of millivolts and microvolts, any oxidation may cause reading inaccuracies and/or reading drift over time.

As another alternative manner of attaching graphene layer 116 to the underlying reference sensor 108 or nutrient sensor 110, electrically conductive transfer tape is used to transfer the graphene layer 116, which may be formed of a LIG sensor formed from Polyimide tape onto the underlying gold pads of reference sensor 108 or nutrient sensor 110. In this situation the sensor themselves would not have any polyimide components as the graphene layer 116, which is LIG, is transferred from a polyimide tape to the underlying gold pads of reference sensor 108 or nutrient sensor 110.

To be clear, graphene and polyimide and Kapton are carbon based layers. As such, what is described herein is a carbon based conductive sensor that is configured to detect the presence of ions through changes in the electrical potential of the sensor. These changes in the electrical potential can be translated in to concentration of the particular sensed nutrient. As such, any form of a carbon based conductive sensor is hereby contemplated for use with the use of graphene, polyimide, Kapton, etc., simply being examples of carbon layers that may be used. That is, in this case, reference sensor or nutrient sensor 110 includes a carbon based layer that facilitates a carbon based conductive sensor wherein the electrical potential changes when ions engage carbon based conductive sensor. Additional forms of a carbon layer that may be used may include biochar, carbon black or any other form of a carbon layer.

Testing Water Quality:

Although some various disclosed embodiments may be primarily described in the context of soil measurements, the embodiments are not so limited. Rather, it is appreciated that the embodiments may be adapted for use in various other sensor applications. As one example, in one or more embodiments, soil moisture and fertility sensor system 10 may be adapted for use for sensing of quality and contents of water. For instance, in one or more arrangements, system 10 may be adapted for testing nutrient levels (e.g., nitrates) in various water sources including but not limited to, for example, tile drainage, irrigation (surface, canal, and/or well), rivers and streams, municipal water, and/or any other water source.

Objectives Met:

From the above discussion it will be appreciated that the soil moisture and nutrient sensor system presented herein improves upon the state of the art.

Specifically, the soil moisture and nutrient sensor system presented in one or more arrangements: is more environmentally friendly than existing systems and methods; is more efficient than existing systems and methods; is safer to use than existing systems and methods; provides comprehensive moisture data across a field or farm; provides comprehensive moisture data at varying depths; provides comprehensive nutrient data across a field or farm; provides comprehensive nutrient data at varying depths; provides real-time data; provides actionable data; provides leading-indicator data; allows a farmer to be proactive instead of reactive; allows a farmer to maximize output; allows a farmer to minimize inputs; allows a farmer to optimize inputs and outputs; gives a farmer unprecedented visibility to soil moisture and nutrients; improves yields; reduces costs; is relatively inexpensive; is simple to use; can be used to sense nutrients for an entire growing season; has replaceable nutrient sensors; is wireless; is battery powered; helps a farmer meet increasingly strict environmental regulations; is easy to use; is easy to implement; has a robust design; provides charts and graphs of soil moisture and soil nutrients; provides a farmer with increased confidence in their decisions; provides accurate soil moisture readings; provides accurate soil nutrient readings; allows for the measurement of multiple nutrients; normalizes moisture and nutrient readings with temperature; provides co-located moisture, temperature and nutrient readings at various depths; is cost effective to use; can be used with any crop; can be used with any nutrient; provides highly repeatable results; has a robust design; provides highly accurate results; has a long useful life; is easy to install; has relatively few components; has a minimum number of parts; minimizes nutrient runoff; is environmentally friendly; improves a farmer's efficiency; saves a farmer time; and/or provides scientific information regarding soil moisture and nutrients, among countless other advantages and improvements.

It will be appreciated by those skilled in the art that other various modifications could be made to the device without parting from the spirit and scope of this disclosure. All such modifications and changes fall within the scope of the claims and are intended to be covered thereby.

What is claimed:

1. A soil moisture and fertility sensor system, comprising:
a probe;
the probe extending a length from an upper end to a lower end;
the probe having a plurality of sensor modules;
wherein the plurality of sensor modules are spaced along the length of the probe;
wherein the plurality of sensor modules include a co-located moisture sensor assembly, a temperature sensor assembly and a fertility sensor assembly;
wherein the probe is configured to be inserted into soil;
wherein when the probe is inserted into soil, the probe makes a moisture measurement, a temperature measurement, and a fertility measurement of the soil at varying depths;
wherein the fertility sensor assembly of the plurality of sensor modules include at least one nutrient sensor,
wherein the at least one nutrient sensor includes a barrier having a selectively permeable membrane.

2. The system of claim 1, wherein the selectively permeable membrane is configured to permit a selected set of materials, ions, nutrients, chemistries, molecules, or constituents to be measured to pass through the selectively permeable membrane while blocking other ions, nutrients, chemistries, molecules, or constituents.

3. The system of claim 1, wherein the barrier includes a layer of material having one or more perforations.

4. The system of claim 1, wherein the barrier includes a layer of material having one or more perforations;
wherein the one or more perforations are micro perforations.

5. A soil moisture and fertility sensor system, comprising:
a probe;
the probe extending a length from an upper end to a lower end;
the probe having a plurality of sensor modules;
wherein the plurality of sensor modules are spaced along the length of the probe;
wherein the plurality of sensor modules include a co-located moisture sensor assembly, a temperature sensor assembly and a fertility sensor assembly;
wherein the probe is configured to be inserted into soil;
wherein when the probe is inserted into soil, the probe makes a moisture measurement, a temperature measurement, and a fertility measurement of the soil at varying depths;
a processing circuit;
wherein the processing circuit is configured to normalize the fertility measurement of one of the plurality of sensor modules based on the temperature measurement of the one of the plurality of sensor modules to determine a normalized fertility measurement;
wherein the processing circuit is configured to normalize the moisture measurement based on the temperature measurement to determine a normalized moisture measurement of the one of the plurality of sensor modules.

6. The system of claim 5, wherein the moisture sensor assembly of the plurality of sensor modules is formed of a capacitance sensor, wherein the capacitance sensor measures the dielectric constant of the soil.

7. A soil moisture and fertility sensor system, comprising:
a probe;
the probe extending a length from an upper end to a lower end;
the probe having a plurality of sensor modules;
wherein the plurality of sensor modules are spaced along the length of the probe;
wherein the probe is configured to be inserted into soil;
wherein when the probe is inserted into soil, the probe makes a moisture measurement and a fertility measurement of the soil at varying depths;
wherein at least one of the plurality of sensor modules includes a moisture sensor assembly and a fertility sensor assembly;
the moisture sensor assembly formed of a capacitance sensor having a positive plate, a negative plate and a space between the positive plate and the negative plate, wherein the fertility sensor assembly is positioned within the space between the positive plate and the negative plate.

8. The system of claim 7, wherein the fertility sensor is positioned within the moisture sensor assembly.

9. The system of claim 7, wherein the fertility sensor assembly includes a reference sensor.

10. The system of claim 7, wherein the fertility sensor assembly includes at least one nutrient sensor.

11. The system of claim 7, wherein the fertility sensor assembly includes at least one nutrient sensor, wherein the at least one nutrient sensor includes a polyimide layer.

12. The system of claim 7, wherein the fertility sensor includes at least one nutrient sensor, wherein the at least one nutrient sensor includes a layer of material having at least one perforation.

13. The system of claim 7, wherein the fertility sensor assembly includes at least one nutrient sensor, wherein the at least one nutrient sensor includes a graphene layer.

14. The system of claim 7, wherein the fertility sensor assembly includes at least one nutrient sensor, wherein the at least one nutrient sensor includes a layer of ceramic or glass that prevents soil adhesion.

15. The system of claim 7, wherein the fertility sensor assembly of the plurality of sensor modules include a cartridge that fits within a receptacle in the probe.

16. A soil moisture and fertility sensor system, comprising:
a plurality of probes;
a gateway;
a database;
the gateway communicatively connected to each of the plurality of probes and the database;
wherein the gateway is configured to receive soil measurement data from each of the plurality of probes;
wherein each of the sensor modules is configured to measure soil measurement data at different depths and communicate the soil measurement data to the gateway;
wherein the gateway is configured to communicate the soil measurement for the different depths received from the plurality of probes to the database.

17. The system of claim 16, further comprising:
a processing circuit communicatively connected to the database;
wherein the process circuit is configured and arranged to evaluate the soil measurement data in the database and identify trends in the soil measurement data.

18. The system of claim 16, further comprising:
a processing circuit communicatively connected to the database;
wherein the process circuit is configured and arranged to evaluate the soil measurement data in the database and predict future soil conditions that will result from a proposed soil treatment specified by a user.

19. The system of claim 16, further comprising at least one additional sensor module;
wherein the at least one additional sensor module is configured to measure soil measurement data from a single soil depth and communicate the soil measurement data to the gateway.

20. A sensor system, comprising:
a probe;
the probe extending a length from an upper end to a lower end;
the probe having a plurality of sensor modules;
wherein the plurality of sensor modules are spaced along the length of the probe;
wherein the plurality of sensor modules include a fertility sensor assembly;
wherein the probe makes a fertility measurement at varying points along the length of the probe;
wherein the fertility sensor assembly of the plurality of sensor modules includes at least one nutrient sensor, wherein the at least one nutrient sensor includes a layer of material having at least one perforation.

21. The system of claim 20, wherein the probe is configured for taking measurements in soil.

22. The system of claim 20, wherein the probe is configured for taking measurements in a body of water.

* * * * *